United States Patent
Brown et al.

(10) Patent No.: US 9,508,537 B2
(45) Date of Patent: Nov. 29, 2016

(54) PHOTO-DISSOCIATION OF PROTEINS AND PEPTIDES IN A MASS SPECTROMETER

(75) Inventors: Jeffery Mark Brown, Hyde (GB); Kevin Giles, Stockport (GB); Daniel James Kenny, Knutsford (GB); Paul Murray, Manchester (GB); Keith Richardson, High Peak (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 14/130,440

(22) PCT Filed: Jul. 6, 2012

(86) PCT No.: PCT/GB2012/051610
§ 371 (c)(1),
(2), (4) Date: May 27, 2014

(87) PCT Pub. No.: WO2013/005061
PCT Pub. Date: Jan. 10, 2013

(65) Prior Publication Data
US 2014/0291501 A1 Oct. 2, 2014

Related U.S. Application Data

(60) Provisional application No. 61/508,265, filed on Jul. 15, 2011.

(30) Foreign Application Priority Data

Jul. 6, 2011 (GB) .................................. 1111560.7

(51) Int. Cl.
*H01J 49/06* (2006.01)
*H01J 49/42* (2006.01)
(Continued)

(52) U.S. Cl.
CPC .......... *H01J 49/062* (2013.01); *H01J 49/0027* (2013.01); *H01J 49/0059* (2013.01);
(Continued)

(58) Field of Classification Search
CPC ............. H01J 49/0027; H01J 49/0059; H01J 49/062; H01J 49/10; H01J 49/26; H01J 49/40; H01J 49/4245; H01J 49/422
USPC ............ 250/288, 282, 281, 287, 423 R, 424; 315/111.81
See application file for complete search history.

(56) References Cited

U.S. PATENT DOCUMENTS 6,621,074 B1  9/2003  Vestal
6,642,516 B1  11/2003  Hansen et al.
(Continued)

FOREIGN PATENT DOCUMENTS

JP  2009/119561  6/2009
WO  9631900  10/1996

OTHER PUBLICATIONS

"Mass Analyzers (Mass Spectrometry)—Chemwiki" downloaded at http://chemwiki.ucdavis.edu/Core/Analytical_Chemistry/Instrumental_Analysis/Mass_Spectrometry/Mass_Spectrometers_(Instrumentation)/Mass_Analyzers_(Mass_Spectrometry), Feb. 12, 2016.*
(Continued)

*Primary Examiner* — Wyatt Stoffa
(74) *Attorney, Agent, or Firm* — Diedericks & Whitelaw, PLC

(57) ABSTRACT

A method of mass spectrometry is disclosed comprising directing first photons from a laser onto ions located within a 2D or linear ion guide or ion trap. The frequency of the first photons is scanned and first photons and/or second photons emitted by the ions are detected. The ions are then mass analyzed using a Time of Flight mass analyzer.

16 Claims, 6 Drawing Sheets

(51) Int. Cl.
*H01J 49/00* (2006.01)
*H01J 49/10* (2006.01)
*H01J 49/26* (2006.01)
*H01J 49/40* (2006.01)

(52) U.S. Cl.
CPC .............. *H01J 49/10* (2013.01); *H01J 49/26* (2013.01); *H01J 49/40* (2013.01); *H01J 49/422* (2013.01); *H01J 49/4245* (2013.01)

(56) References Cited

U.S. PATENT DOCUMENTS

| | | | |
|---|---|---|---|
| 6,717,137 B2* | 4/2004 | Hofstadler | H01J 49/0059 250/288 |
| 6,828,550 B2 | 12/2004 | Griffey et al. | |
| 7,532,320 B2 | 5/2009 | Neiss et al. | |
| 7,618,806 B2 | 11/2009 | Reilly et al. | |
| 7,718,959 B2 | 5/2010 | Franzen et al. | |
| 7,807,963 B1* | 10/2010 | Bier | H01J 49/422 250/281 |
| 7,816,644 B2 | 10/2010 | Fischer et al. | |
| 7,829,845 B2 | 11/2010 | Deguchi et al. | |
| 7,928,363 B2 | 4/2011 | Bateman et al. | |
| 8,101,910 B2 | 1/2012 | Loboda | |
| 8,106,353 B2* | 1/2012 | Loboda | H01J 49/0045 250/281 |
| 8,395,112 B1* | 3/2013 | Bier | G01N 21/53 250/281 |
| 8,524,502 B2 | 9/2013 | Basile et al. | |
| 8,546,755 B2* | 10/2013 | Hoyes | G01N 27/622 250/285 |
| 8,581,182 B2* | 11/2013 | Giles | H01J 49/062 250/282 |
| 8,592,752 B2 | 11/2013 | Gorenstein et al. | |
| 8,916,834 B2 | 12/2014 | Lane | |
| 2002/0104962 A1* | 8/2002 | Danno | G01N 27/622 250/288 |
| 2003/0016926 A1* | 1/2003 | Hofstadler | H01J 49/0059 385/125 |
| 2003/0180957 A1 | 9/2003 | Koopmann et al. | |
| 2007/0046934 A1* | 3/2007 | Roy | G01J 3/4338 356/318 |
| 2009/0242753 A1 | 10/2009 | Dugourd et al. | |
| 2009/0256067 A1* | 10/2009 | Syage | H01J 49/426 250/281 |
| 2010/0065733 A1* | 3/2010 | Bateman | H01J 49/004 250/282 |
| 2010/0123075 A1* | 5/2010 | Dantus | H01J 49/0059 250/282 |
| 2010/0207023 A1* | 8/2010 | Loboda | H01J 49/0045 250/282 |
| 2010/0301205 A1* | 12/2010 | Thomson | H01J 49/0045 250/283 |
| 2011/0168883 A1* | 7/2011 | Furuhashi | H01J 49/0059 250/288 |
| 2011/0204221 A1 | 8/2011 | Satake et al. | |
| 2012/0032073 A1 | 2/2012 | Rand et al. | |
| 2014/0151546 A1* | 6/2014 | Li | H01J 49/062 250/282 |
| 2014/0224974 A1* | 8/2014 | Kenny et al. | 250/282 |
| 2015/0034814 A1* | 2/2015 | Brown | H01J 49/164 250/282 |

OTHER PUBLICATIONS

Agarwal et al., "*Direct Elucidation of di-sulfide Bond Partners Using Ultraviolet Photo dissociation Mass Spectrometry*", University of California at Riverside, ASMS, 2011.
Horn et al., "*Kinetic Intermediates in the Folding of Gaseous Protein Ions Characterized by Electron Capture Dissociation Mass Spectrometry*", J. Am. Chem Soc., vol. 123, pp. 9792-9799, 2001.
Jones et al., "*Electron Capture Dissociation Mass Spectrometry of Tyrosine Nitrated Peptides*", American Society of Mass Spectrometry, vol. 21, No. 2, pp. 268-277, 2010.
Lin et al., "*Probing the Gas-Phase Folding Kinetics of Peptide Ions by IR Activated DR-ECD*", American Society for Mass Spectrometry, vol. 19, pp. 780-789, 2008.
Nishikaze et al., "*Influence of Charge State and Amino Acid Composition on Hydrogen Transfer in Electron Capture Dissociation of Peptides*", American Society of Mass Spectrometry, vol. 21, pp. 1979-1988, 2010.
Savitski et al., "*Hydrogen Rearrangement to and from Radical Z Fragments in Electron Capture Dissociation of Peptides*", American Society for Mass Spectrometry, vol. 18, pp. 113-120, 2007.
"*Tandem-in-Space Mass Spectrometry (MS/MS)*", Introduction to Mass Spectrometry: Instrumentation, Applications, and Strategies for Data Interpretation, pp. 186-196, 2007.
Metz, "*Optical Spectroscopy and Photo Dissociation Dynamics of Multiply Charged Ions*", International Journal of Mass Spectrometry, vol. 235, No. 2, pp. 131-143, 2004.
Welling, "*Ion/Molecule Reactions, Mass Spectrometry and Optical Spectroscopy in a Linear Ion Trap*", International Journal of Mass Spectrometry, vol. 172, No. 1-2, pp. 95-114, 1998.
Di Fidio et al., "*Quantum Control of Light and Motion with a Trapped Ion in a Leaky Cavity*", Journal of Optics, vol. 4, No. 5, pp. 342-346, 2002.
Russo et al., "*Raman Spectroscopy of a Single Ion Coupled to a High-Finesse Cavity*", Applied Physics, vol. 2, pp. 205-212, 2009.

* cited by examiner

Fig. 3a
_Prior Art_
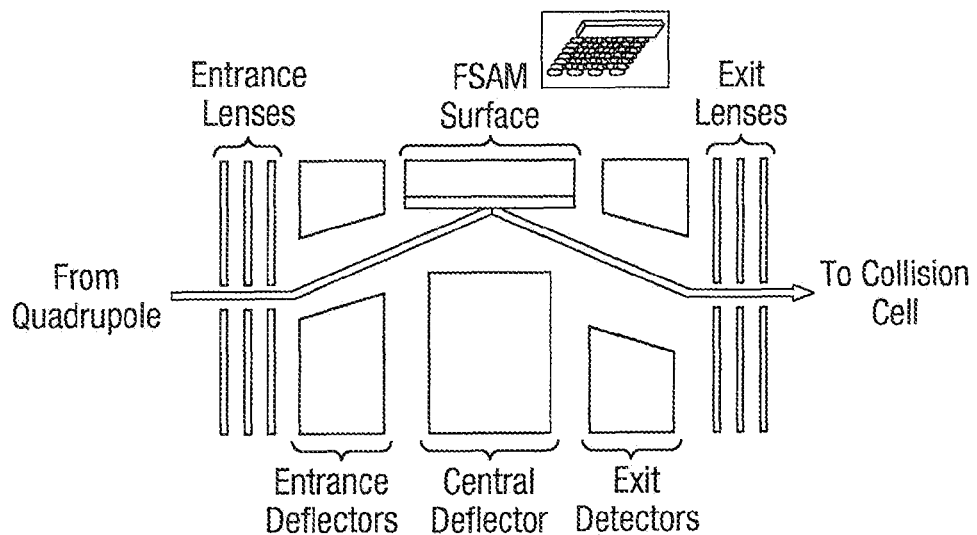

PHOTO-DISSOCIATION OF PROTEINS AND PEPTIDES IN A MASS SPECTROMETER

CROSS REFERENCE TO RELATED APPLICATIONS

This application is the National Stage of International Application No. PCT/GB2012/051610, filed 6 Jul. 2012, which claims priority from and the benefit of U.S. Provisional Patent Application Ser. No. 61/508,265 filed on 15 Jul. 2011 and United Kingdom Patent Application No. 1111560.7 filed on 6 Jul. 2011. The entire contents of these applications are incorporated herein by reference.

BACKGROUND OF THE INVENTION

According to the present invention there is provided a mass spectrometer and a method of mass spectrometry.

Disulfide (S—S) bond mapping is crucial in the development and quality control of biopharmaceuticals since these bonds have a direct effect on protein structure and function. Enzymatic digestion of native proteins followed by LC-MS/MS or LC-MS$^E$ analysis can provide information on the location of S—S bonds. However, the analysis is complicated by a combinatoric explosion of possible linkages especially when the protein is cysteine-rich or when other variable post translational modifications are involved. Another problem for data analysis is the large number of charges carried by peptide complexes.

The preferential cleavage of disulfide bonds (c.f. C—S bonds) by a 248 nm laser was noted by Bookwalter in 1995.

It is also known to use a 266 nm YAG laser to preferentially cleave peptide S—S bonds of peptide complex ions held in an on trap. It is also known to mass analyse the resulting peptide ions which comprise the precursor ions and the individual peptide chains (with a fairly even charge state split).

FIG. 1 illustrates the known process of cleaving a single disulfide bond of a peptide complex to form two peptide sequences. In a similar manner, a peptide complex of three peptide sequences A,B,C linked by two disulfide bonds (i.e. A-B-C) will yield precursor ions (ABC), peptide pairs (AB,BC) and individual peptide chains (A,B,C). By way of contrast, Collision Induced Dissociation ("CID") fragmentation of a peptide complex produces mass spectra containing many fragments which are much harder to interpret.

It is also known that labile phosphorylation modifications are preserved when peptide complexes are subjected to photo-dissociation i.e. photo-dissociation selectively cleaves the S—S bond without losing the phosphorylation.

It is desired to provide an improved method of mass spectrometry and an improved mass spectrometer.

SUMMARY OF THE INVENTION

According to an aspect of the present invention there is provided a method of mass spectrometry comprising:

automatically and repeatedly performing multiple cycles of operation, wherein a cycle of operation comprises the steps of:

(i) mass analysing first ions;

(ii) exposing the first ions to a first photo-dissociation device and/or a first photo-activation device to form a plurality of second ions and mass analysing the second ions; and (iii) exposing the first ions to a first photo-dissociation device and/or a first photo-activation device to form a plurality of second ions, fragmenting the second ions or exposing the second ions to a second photo-dissociation device and/or a second photo-activation device to form a plurality of third ions and mass analysing the third ions.

In at least one cycle of operation, in at least some cycles of operation or in each cycle of operation step (i) is preferably performed prior to or after step (ii) or (iii).

In at least one cycle of operation, in at least some cycles of operation or in each cycle of operation step (ii) is preferably performed prior to or after step (i) or (iii).

In at least one cycle of operation, in at least some cycles of operation or in each cycle of operation step (iii) is preferably performed prior to or after step (i) or (ii).

At least one cycle of operation, at least some cycles of operation or each cycle of operation preferably further comprises the step of:

(iv) fragmenting the first ions or exposing the first ions to a second photo-dissociation device and/or a second photo-activation device to form a plurality of fourth ions and mass analysing the fourth ions.

In at least one cycle of operation, in at least some cycles of operation or in each cycle of operation step (iv) is preferably performed prior to or after step (i), (ii) or (iii)

The method preferably comprises a Data Independent Acquisition ("DIA") method.

According to an aspect of the present invention there is provided a method of mass spectrometry comprising:

automatically and repeatedly performing multiple cycles of operation, wherein a cycle of operation comprises the steps of:

(a) mass analysing first ions; and (b) fragmenting the first ions or exposing the first ions to a second photo-dissociation device and/or a second photo-activation device to form a plurality of fourth ions and mass analysing the fourth ions;

wherein if a determination is made that the first ions and/or the fourth ions comprise ions of interest then the method further comprises:

(c) exposing the first ions to a first photo-dissociation device and/or a first photo-activation device to form a plurality of second ions and mass analysing the second ions; and/or (d) exposing the first ions to a first photo-dissociation device and/or a first photo-activation device to form a plurality of second ions, fragmenting the second ions or exposing the second ions to the second photo-dissociation device and/or a second photo-activation device to form a plurality of third ions and mass analysing the third ions.

The method preferably comprises a Data Directed Acquisition ("DDA") method.

According to an aspect of the present invention there is provided a method of mass spectrometry comprising:

automatically and repeatedly performing multiple cycles of operation, wherein a cycle of operation comprises the steps of:

(i) mass analysing first ions;

(ii) fragmenting the first ions or exposing the first ions to a first photo-dissociation device and/or a first photo-activation device to form a plurality of fifth ions and mass analysing the fifth ions;

(iii) fragmenting the first ions or exposing the first ions to a first photo-dissociation device and/or a first photo-activation device to form a plurality of fifth ions, exposing the fifth ions to a second photo-dissociation device and/or a second photo-activation device to form a plurality of sixth ions and mass analysing the sixth ions.

According to an aspect of the present invention there is provided a method of mass spectrometry comprising:

automatically and repeatedly performing multiple cycles of operation, wherein a cycle of operation comprises the steps of:

(a) mass analysing first ions; and (b) exposing the first ions to a second photo-dissociation device and/or a second photo-activation device to form a plurality of seventh ions and mass analysing the seventh ions;

wherein if a determination is made that the first ions and/or the seventh ions comprise ions of interest then the method further comprises:

(c) fragmenting the first ions or exposing the first ions to a first photo-dissociation device and/or a first photo-activation device to form a plurality of fifth ions and mass analysing the fifth ions; and/or (d) fragmenting the first ions or exposing the first ions to a first photo-dissociation device and/or a first photo-activation device to form a plurality of fifth ions, exposing the fifth ions to the second photo-dissociation device and/or a second photo-activation device to form a plurality of sixth ions and mass analysing the sixth ions.

The method preferably further comprises ionising an eluent eluting from a liquid chromatography device to form a plurality of the first ions.

The step of exposing ions to the first photo-dissociation device and/or the second photo-dissociation device and/or the first photo-activation device and/or the second photo-activation device preferably comprises directing a laser beam on to the ions whilst the ions are confined radially and/or axially within an ion guide.

The step of exposing ions to the first photo-dissociation device and/or the second photo-dissociation device preferably comprises irradiating the ions with photons emitted from a mercury lamp.

The method preferably further comprises operating the mercury lamp at atmospheric pressure or sub-atmospheric pressure.

The laser beam and/or the photons preferably have a wavelength in the range <100 nm, 100-200 nm, 200-300 nm, 300-400 nm, 400-500 nm, 500-600 nm, 600-700 nm, 700-800 nm, 800-900 nm, 900-1000 nm, 1-2 µm, 2-3 µm, 3-4 µm, 4-5 µm, 5-6 µm, 6-7 µm, 7-8 µm, 8-9 µm, 9-10 µm, 10-11 µm and >11 µm.

The step of exposing ions to the first photo-dissociation device and/or the second photo-dissociation device preferably comprises substantially simultaneously generating and photo-dissociating ions in an ion source.

The ion source preferably comprises a Matrix Assisted Laser Desorption Ionisation ("MALDI") ion source.

The step of exposing ions to the first photo-dissociation device and/or the second photo-dissociation device preferably causes cleavage of one or more disulfide bonds in the ions.

The step of exposing ions to the first photo-activation device and/or the second photo-activation device preferably causes unfolding of the ions or a change in conformation of the ions.

The step of fragmenting ions preferably comprises fragmenting the ions by: (i) Collisional Induced Dissociation ("CID"); (ii) Surface Induced Dissociation ("SID"); (iii) Electron Transfer Dissociation ("ETD"); (iv) Electron Capture Dissociation ("ECD"); (v) Electron Collision or Impact Dissociation; (vi) Photo Induced Dissociation ("PID"); (vii) Laser Induced Dissociation; (viii) infrared radiation induced dissociation; (ix) ultraviolet radiation induced dissociation; (x) using a nozzle-skimmer interface; (xi) using an in-source; (xii) using an in-source Collision Induced Dissociation; (xiii) using a thermal or temperature source; (xiv) using an induced electric field; (xv) using an induced magnetic field; (xvi) using enzyme digestion or enzyme degradation; (xvii) using an ion-ion reaction; (xviii) using an ion-molecule reaction; (xix) using an ion-atom reaction; (xx) using an ion-metastable ion reaction; (xxi) using an ion-metastable molecule reaction; (xxii) using an ion-metastable atom reaction; (xxiii) using an ion-ion reaction for reacting ions to form adduct or product ions; (xxiv) using an ion-molecule reaction for reacting ions to form adduct or product ions; (xxv) using an ion-atom reaction for reacting ions to form adduct or product ions; (xxvi) using an ion-metastable ion reaction for reacting ions to form adduct or product ions; (xxvii) using an ion-metastable molecule reaction for reacting ions to form adduct or product ions; (xxviii) using an ion-metastable atom reaction for reacting ions to form adduct or product ions; (xxix) Electron Ionisation Dissociation ("EID"); and (xxx) Electron Detachment Dissociation ("EDD") wherein electrons are irradiated onto negatively charged parent or analyte ions to cause the parent or analyte ions to fragment.

The method preferably further comprises mass filtering the first ions.

The method preferably further comprises separating the first ions and/or the second ions according to their ion mobility or their differential ion mobility.

According to an aspect of the present invention there is provided a mass spectrometer comprising:

a first photo-dissociation device and/or first photo-activation device;

a fragmentation device or a second photo-dissociation device and/or second photo-activation device;

a mass analyser; and a control system arranged and adapted to automatically and repeatedly perform multiple cycles of operation, wherein a cycle of operation comprises the steps of:

(i) mass analysing first ions;

(ii) exposing the first ions to the first photo-dissociation device and/or first photo-activation device to form a plurality of second ions and mass analysing the second ions; and (iii) exposing the first ions to the first photo-dissociation device and/or first photo-activation device to form a plurality of second ions, fragmenting the second ions in the fragmentation device or exposing the second ions to the second photo-dissociation device and/or second photo-activation device to form a plurality of third ions and mass analysing the third ions.

According to an aspect of the present invention there is provided a mass spectrometer comprising:

a first photo-dissociation device and/or first photo-activation device;

a fragmentation device or a second photo-dissociation device and/or second photo-activation device;

a mass analyser; and a control system arranged and adapted to automatically and repeatedly perform multiple cycles of operation, wherein a cycle of operation comprises the steps of:

(a) mass analysing first ions; and (b) fragmenting the first ions in the fragmentation device or exposing the first ions to the second photo-dissociation device and/or second photo-activation device to form a plurality of fourth ions and mass analysing the fourth ions;

wherein if, in use, a determination is made that the first ions and/or the fourth ions comprise ions of interest then the control system is further arranged and adapted:

(c) to cause the first ions to be exposed to the first photo-dissociation device and/or second photo-activation device to form a plurality of second ions and to cause the mass analyser to mass analyse the second ions; and/or (d) to cause the first ions to be exposed to the first photo-dissociation device and/or first photo-activation device to form a plurality of second ions, to cause the second ions to be fragmented by the fragmentation device or to cause the second ions to be exposed to the second photo-dissociation device and/or second photo-activation device to form a plurality of third ions and to cause the mass analyser to mass analyse the third ions.

According to an aspect of the present invention there is provided a mass spectrometer comprising:

a fragmentation device or first photo-dissociation device and/or first photo-activation device;

a second photo-dissociation device and/or second photo-activation device;

a mass analyser; and a control system arranged and adapted to automatically and repeatedly perform multiple cycles of operation, wherein a cycle of operation comprises the steps of:

(i) mass analysing first ions;

(ii) fragmenting the first ions in the fragmentation device or exposing the first ions to the first photo-dissociation device and/or first photo-activation device to form a plurality of fifth ions and mass analysing the fifth ions;

(iii) fragmenting the first ions in the fragmentation device or exposing the first ions to the first photo-dissociation device and/or first photo-activation device to form a plurality of fifth ions, exposing the fifth ions to the second photo-dissociation device and/or second photo-activation device to form a plurality of sixth ions and mass analysing the sixth ions.

According to an aspect of the present invention there is provided a mass spectrometer comprising:

a fragmentation device or first photo-dissociation device and/or first photo-activation device;

a second photo-dissociation device and/or second photo-activation device;

a mass analyser; and a control system arranged and adapted to automatically and repeatedly perform multiple cycles of operation, wherein a cycle of operation comprises the steps of:

(a) mass analysing first ions; and (b) exposing the first ions to the second photo-dissociation device and/or second photo-activation device to form a plurality of seventh ions and mass analysing the seventh ions;

wherein, in use, if a determination is made that the first ions and/or the seventh ions comprise ions of interest then the control system is further arranged and adapted to:

(c) to cause the first ions to be fragmented in the fragmentation device or to cause the first ions to be exposed to the first photo-dissociation device and/or first photo-activation device to form a plurality of fifth ions and to cause the mass analyser to mass analyse the fifth ions; and/or (d) to cause the first ions to be fragmented in the fragmentation device or to cause the first ions to be exposed to the first photo-dissociation device and/or first photo-activation device to form a plurality of fifth ions, to cause the fifth ions to be exposed to the second photo-dissociation device and/or second photo-activation device to form a plurality of sixth ions and to cause the mass analyser to mass analyse the sixth ions.

The first photo-dissociation device and/or the second photo-dissociation device and/or the first photo-activation device and/or the second photo-activation device preferably comprises a laser and an ion guide wherein the laser is arranged and adapted to direct a laser beam on to the ions, in use, whilst the ions are confined radially and/or axially within the ion guide.

The first photo-dissociation device and/or the second photo-dissociation device preferably comprise a mercury lamp arranged and adapted to irradiate the ions, in use, with photons.

The mercury lamp is preferably arranged and adapted to be operated at atmospheric pressure or sub-atmospheric pressure.

The laser beam and/or the photons preferably have a wavelength in the range <100 nm, 100-200 nm, 200-300 nm, 300-400 nm, 400-500 nm, 500-600 nm, 600-700 nm, 700-800 nm, 800-900 nm, 900-1000 nm, 1-2 μm, 2-3 μm, 3-4 μm, 4-5 μm, 5-6 μm, 6-7 μm, 7-8 μm, 8-9 μm, 9-10 μm, 10-11 μm and >11 μm.

The first photo-dissociation device and/or the second photo-dissociation device preferably comprises an ion source arranged and adapted to substantially simultaneously generate and photo-dissociate ions.

The ion source preferably comprises a Matrix Assisted Laser Desorption Ionisation ("MALDI") ion source.

The fragmentation device is preferably selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; (xxix) an Electron Ionisation Dissociation ("EID") fragmentation device; and (xxx) an Electron Detachment Dissociation ("EDD") device wherein electrons are irradiated onto negatively charged parent or analyte ions to cause the parent or analyte ions to fragment.

The mass spectrometer preferably further comprises a mass filter arranged and adapted to mass filter the first ions.

The mass spectrometer preferably further comprises an ion mobility spectrometer or separator arranged and adapted to separate the first ions and/or the second ions according to their ion mobility.

The mass spectrometer preferably further comprises a differential ion mobility spectrometer or separator or Field Asymmetric Ion Mobility Spectrometry ("FAIMS") device arranged and adapted to separate the first ions and/or the second ions according to their differential ion mobility and/or rate of change of ion mobility with electric field strength.

According to an aspect of the present invention there is provided a method of mass spectrometry comprising:

subjecting biomolecular ions to Hydrogen-Deuterium exchange to form first ions; and then causing the first ions to at least partially unfold or alter their conformation to form second ions by either:

(i) subjecting the first ions or ions derived from the first ions to IR, visible or UV photo-activation; and/or (ii) exposing the first ions or ions derived from the first ions to acidic vapours or UV supercharging the ions; and/or (iii) subjecting the first ions or ions derived from the first ions to IR, visible or UV photo-dissociation According to an aspect of the present invention there is provided a method of mass spectrometry comprising:

causing biomolecular ions to at least partially unfold or alter their conformation to form first ions by either:

(i) subjecting the biomolecular ions or ions derived from the biomolecular ions to IR, visible or UV photo-activation; and/or (ii) exposing the biomolecular ions or ions derived from the biomolecular ions to acidic vapours or supercharging the ions; and/or (iii) subjecting the biomolecular ions or ions derived from the biomolecular ions to IR, visible or UV photo-dissociation; and then subjecting the first ions to Hydrogen-Deuterium exchange to form second ions.

The step of subjecting the biomolecular ions or first ions to photo-dissociation preferably results in cleaving one or more disulfide bonds in the ions.

The step of subjecting the biomolecular ions or first ions to photo-dissociation preferably comprises fragmenting the ions.

The method preferably further comprises fragmenting at least some of the second ions to form third ions.

The step of fragmenting at least some of the second ions preferably comprises fragmenting at least some of the second ions by: (i) Electron Transfer Dissociation ("ETD"); and/or (ii) by IR, visible or UV photo-dissociation; and/or (iii) by Collision Induced Dissociation ("CID").

The method preferably further comprises subjecting at least some of the second ions to photo-dissociation to form third ions.

The method preferably further comprises:

separating at least some of the first ions and/or at least some of the second ions and/or at least some of the third ions temporally according to their ion mobility or differential ion mobility.

The biomolecular ions preferably comprise protein ions or native protein ions.

The step of causing the biomolecular ions or first ions to at least partially unfold or alter their conformation is preferably performed at a pressure selected from the group consisting of: (i) >100 mbar; (ii) >10 mbar; (iii) >1 mbar; (iv) >0.1 mbar; (v) >$10^{-2}$ mbar; (vi) >$10^{-3}$ mbar; (vii) >$10^{-4}$ mbar; (viii) >$10^{-5}$ mbar; (ix) >$10^{-6}$ mbar; (x) <100 mbar; (xi) <10 mbar; (xii) <1 mbar; (xiii) <0.1 mbar; (xiv) <$10^{-2}$ mbar; (xv) <$10^{-3}$ mbar; (xvi) <$10^{-4}$ mbar; (xvii) <$10^{-5}$ mbar; (xviii) <$10^{-6}$ mbar; (xix) 10-100 mbar; (xx) 1-10 mbar; (xxi) 0.1-1 mbar; (xxii) $10^{-2}$ to $10^{-1}$ mbar; (xxiii) $10^{-3}$ to $10^{-2}$ mbar; (xxiv) $10^{-4}$ to $10^{-3}$ mbar; and (xxv) $10^{-5}$ to $10^{-4}$ mbar.

The step of causing the biomolecular ions or first ions to at least partially unfold or alter their conformation is preferably performed at atmospheric pressure.

The step of subjecting the biomolecular ions or first ions to photo-activation preferably comprises directing photons on to the ions, wherein the photons have a wavelength in the range <100 nm, 100-200 nm, 200-300 nm, 300-400 nm, 400-500 nm, 500-600 nm, 600-700 nm, 700-800 nm, 800-900 nm, 900-1000 nm, 1-2 µm, 2-3 µm, 3-4 µm, 4-5 µm, 5-6 µm, 6-7 µm, 7-8 µm, 8-9 µm, 9-10 µm, 10-11 µm and >11 µm.

According to an aspect of the present invention there is provided a mass spectrometer comprising:

a device arranged and adapted to subject biomolecular ions to Hydrogen-Deuterium exchange to form first ions; and a device arranged and adapted to cause the first ions to at least partially unfold or alter their conformation to form second ions by either:

(i) subjecting the first ions or ions derived from the first ions to IR, visible or UV photo-activation; and/or (ii) exposing the first ions or ions derived from the first ions to acidic vapours or supercharging the ions; and/or (iii) subjecting the first ions or ions derived from the first ions to IR, visible or UV photo-dissociation.

According to an aspect of the present invention there is provided a mass spectrometer comprising:

a device arranged and adapted to cause biomolecular ions to at least partially unfold or alter their conformation to form first ions by either:

(i) subjecting the biomolecular ions or ions derived from the biomolecular ions to IR, visible or UV photo-activation; and/or (ii) exposing the biomolecular ions or ions derived from the biomolecular ions to acidic vapours or supercharging the ions; and/or (iii) subjecting the biomolecular ions or ions derived from the biomolecular ions to IR, visible or UV photo-dissociation; and a device arranged and adapted to subject the first ions to Hydrogen-Deuterium exchange to form second ions.

According to an aspect of the present invention there is provided a method of mass spectrometry comprising:

directing first photons from a laser onto ions located within a 2D or linear ion guide or ion trap;

scanning or varying the frequency of the first photons; and detecting the first photons and/or detecting second photons emitted by the ions.

The method preferably further comprises mass analysing the ions using a Time of Flight mass analyser.

According to an aspect of the present invention there is provided a method of mass spectrometry comprising:

illuminating ions located within a 2D or linear ion guide or ion trap with broadband illumination;

scanning or varying a transmission property of an optical filter; and detecting photons transmitted by the optical filter.

The method preferably further comprises mass analysing the ions using a Time of Flight mass analyser.

The method preferably further comprises temporally separating the ions according to their ion mobility.

The step of temporally separating the ions according to their ion mobility is preferably performed prior to and/or subsequent to locating the ions within the ion guide or ion trap.

The method preferably further comprises confining the ions radially and/or axially within the ion guide or ion trap.

The ion guide or ion trap is preferably selected from the group comprising:

(a) an ion tunnel ion guide comprising a plurality of electrodes, each electrode comprising one or more apertures through which ions are transmitted in use;

(b) an ion funnel ion guide comprising a plurality of electrodes, each electrode comprising one or more apertures through which ions are transmitted in use and wherein a width or diameter of an ion guiding region formed within the ion funnel ion guide increases or decreases along the axial length of the ion guide;

(c) a conjoined ion guide comprising: (i) a first ion guide section comprising a plurality of electrodes each having an aperture through which ions are transmitted and wherein a first ion guiding path is formed within the first ion guide section; and (ii) a second ion guide section comprising a plurality of electrodes each having an aperture through which ions are transmitted and wherein a second ion guiding path is formed within the second ion guide section, wherein a radial pseudo-potential barrier is formed between the first ion guiding path and the second ion guiding path;

(d) a multipole or segmented multipole rod set; or (e) a planar ion guide comprising a plurality of planar electrodes arranged parallel to or orthogonal to a longitudinal axis of the ion guide.

The method preferably further comprises directing the first photons in a direction which is substantially co-axial and/or parallel with a longitudinal axis of the ion guide or ion trap.

The method preferably further comprises directing the first photons in a direction which is substantially orthogonal to a longitudinal axis of the ion guide or ion trap.

The method preferably further comprises generating one or more absorption spectra.

The method preferably further comprises generating one or more emission spectra.

The method preferably further comprises determining one or more properties of the ions from detecting the first photons and/or the second photons.

The method preferably further comprises maintaining the ion guide or ion trap at a pressure selected from the group consisting of: (i) >100 mbar; (ii) >10 mbar; (iii) >1 mbar; (iv) >0.1 mbar; (v) >$10^{-2}$ mbar; (vi) >$10^{-3}$ mbar; (vii) >$10^{-4}$ mbar; (viii) >$10^{-5}$ mbar; (ix) >$10^{-6}$ mbar; (x) <100 mbar; (xi) <10 mbar; (xii) <1 mbar; (xii) <0.1 mbar; (xiv) <$10^{-2}$ mbar; (xv) <$10^{-3}$ mbar; (xvi) <$10^{-4}$ mbar; (xvii) <$10^{-5}$ mbar; (xviii) <$10^{-6}$ mbar; (xix) 10-100 mbar; (xx) 1-10 mbar; (xxi) 0.1-1 mbar; (xxii) $10^{-2}$ to $10^{-1}$ mbar; (xxiii) $10^{-3}$ to $10^{-2}$ mbar; (xxiv) $10^{-4}$ to $10^{-3}$ mbar; and (xxv) $10^{-5}$ to $10^{-4}$ mbar.

The first photons preferably have a wavelength in the range <100 nm, 100-200 nm, 200-300 nm, 300-400 nm, 400-500 nm, 500-600 nm, 600-700 nm, 700-800 nm, 800-900 nm, 900-1000 nm, 1-2 µm, 2-3 µm, 3-4 µm, 4-5 µm, 5-6 µm, 6-7 µm, 7-8 µm, 8-9 µm, 9-10 µm, 10-11 µm and >11 µm.

According to an aspect of the present invention there is provided a mass spectrometer comprising:

a 2D or linear ion guide or ion trap;

a laser arranged and adapted to direct first photons onto ions located, in use, within the 2D or linear ion guide or ion trap;

a device arranged and adapted to scan or vary the frequency of the first photons; and a detector for detecting the first photons and/or a detector for detecting second photons emitted by the ions.

The mass spectrometer preferably further comprises a Time of Flight mass analyser.

According to an aspect of the present invention there is provided a mass spectrometer comprising:

a 2D or linear ion guide or ion trap;

a broadband illumination source arranged and adapted to illuminate ions located, in use, within the 2D or linear ion guide or ion trap with broadband illumination;

a device arranged and adapted to scan or vary a transmission property of an optical filter; and a detector for detecting photons transmitted by the optical filter.

The mass spectrometer preferably further comprises a Time of Flight mass analyser.

The mass spectrometer preferably further comprises a device for temporally separating the ions according to their ion mobility.

The device for temporally separating the ions according to their ion mobility is preferably arranged upstream of and/or downstream of the ion guide or ion trap.

The ion guide or on trap is preferably selected from the group comprising:

(a) an ion tunnel ion guide comprising a plurality of electrodes, each electrode comprising one or more apertures through which ions are transmitted in use;

(b) an ion funnel ion guide comprising a plurality of electrodes, each electrode comprising one or more apertures through which ions are transmitted in use and wherein a width or diameter of an ion guiding region formed within the ion funnel ion guide increases or decreases along the axial length of the ion guide;

(c) a conjoined ion guide comprising: (i) a first ion guide section comprising a plurality of electrodes each having an aperture through which ions are transmitted and wherein a first ion guiding path is formed within the first ion guide section; and (ii) a second ion guide section comprising a plurality of electrodes each having an aperture through which ions are transmitted and wherein a second ion guiding path is formed within the second ion guide section, wherein a radial pseudo-potential barrier is formed between the first ion guiding path and the second ion guiding path;

(d) a multipole or segmented multipole rod set; or (e) a planar ion guide comprising a plurality of planar electrodes arranged parallel to or orthogonal to a longitudinal axis of the ion guide.

The mass spectrometer preferably further comprises a device for directing the first photons in a direction which is substantially co-axial and/or parallel with a longitudinal axis of the ion guide or ion trap.

The mass spectrometer preferably further comprises a device for directing the first photons in a direction which is substantially orthogonal to a longitudinal axis of the ion guide or ion trap.

The mass spectrometer preferably further comprises a control system which is arranged and adapted to generate one or more absorption spectra.

The mass spectrometer preferably further comprises a control system which is arranged and adapted to generate one or more emission spectra.

The mass spectrometer preferably further comprises a control system which is arranged and adapted to determine one or more properties of the ions from detecting the first photons and/or the second photons.

The mass spectrometer preferably further comprises a device arranged and adapted to maintain the ion guide or ion trap at a pressure selected from the group consisting of: (1) >100 mbar; (ii) >10 mbar; (iii) >1 mbar; (iv) >0.1 mbar; (v) >$10^{-2}$ mbar; (vi) >$10^{-3}$ mbar; (vii) >$10^{-4}$ mbar; (viii) >$10^{-5}$ mbar; (ix) >$10^{-6}$ mbar; (x) <100 mbar; (xi) <10 mbar; (xii) <1 mbar; (xiii) <0.1 mbar; (xiv) <$10^{-2}$ mbar; (xv) <$10^{-3}$ mbar; (xvi) <$10^{-4}$ mbar; (xvii) <$10^{-5}$ mbar; (xviii) <$10^{-6}$ mbar; (xix) 10-100 mbar; (xx) 1-10 mbar; (xxi) 0.1-1 mbar; (xxii) $10^{-2}$ to $10^{-1}$ mbar; (xxiii) $10^{-3}$ to $10^{-2}$ mbar; (xxiv) $10^{-4}$ to $10^{-3}$ mbar; and (xxv) $10^{-5}$ to $10^{-4}$ mbar.

The laser is preferably arranged and adapted to emit first photons having a wavelength in the range <100 nm, 100-200 nm, 200-300 nm, 300-400 nm, 400-500 nm, 500-600 nm, 600-700 nm, 700-800 nm, 800-900 nm, 900-1000 nm, 1-2 μm, 2-3 μm, 3-4 μm, 4-5 μm, 5-6 μm, 6-7 μm, 7-8 μm, 8-9 μm, 9-10 μm, 10-11 μm and >11 μm.

According to an aspect of the present invention there is provided a method comprising:

providing a conjoined ion guide or ion trap comprising: (i) a first ion guide section comprising a plurality of electrodes each having an aperture through which ions are transmitted and wherein a first ion guiding path is formed within the first ion guide section; and (ii) a second ion guide section comprising a plurality of electrodes each having an aperture through which ions are transmitted and wherein a second ion guiding path is formed within the second ion guide section, wherein a radial pseudo-potential barrier is formed between the first ion guiding path and the second ion guiding path; and directing a laser beam along at least part of the axial length of the first ion guide section and/or the second ion guide section.

The method preferably further comprises locating ions within the first ion guide section and/or the second ion guide section.

The method preferably further comprises subjecting the ions to photo-dissociation.

The photo-dissociation preferably causes cleavage of one or more disulfide bonds of the ions.

The method preferably further comprises subjecting the ions to photo-activation.

The photo-activation preferably causes unfolding of the ions or a change in conformation of the ions.

The method preferably further comprises performing ion spectroscopy.

The laser beam preferably comprises first photons, the method further comprising scanning or varying the frequency of the first photons.

The method preferably further comprises detecting the first photons and/or detecting second photons emitted by the ions.

The method preferably further comprises mass analysing the ions using a Time of Flight mass analyser.

The method preferably further comprises temporally separating the ions according to their ion mobility.

The step of temporally separating the ions according to their ion mobility is preferably performed prior to and/or subsequent to locating the ions within the ion guide or ion trap.

The method preferably further comprises confining the ions radially and/or axially within the ion guide or ion trap.

The method preferably further comprises generating one or more absorption spectra.

The method preferably further comprises generating one or more emission spectra.

The method preferably further comprises determining one or more properties of the ions from detecting the first photons and/or the second photons.

The method preferably further comprises maintaining the ion guide or ion trap at a pressure selected from the group consisting of: (i) >100 mbar; (ii) >10 mbar; (iii) >1 mbar; (iv) >0.1 mbar; (v) >$10^{-2}$ mbar; (vi) >$10^{-3}$ mbar; (vii) >$10^{-4}$ mbar; (viii) >$10^{-5}$ mbar; (ix) >$10^{-6}$ mbar; (x) <100 mbar; (xi) <10 mbar; (xii) <1 mbar; (xiii) <0.1 mbar; (xiv) <$10^{-2}$ mbar; (xv) <$10^{-3}$ mbar; (xvi) <$10^{-4}$ mbar; (xvii) <$10^{-5}$ mbar; (xviii) <$10^{-6}$ mbar; (xix) 10-100 mbar; (xx) 1-10 mbar; (xxi) 0.1-1 mbar; (xxii) $10^{-2}$ to $10^{-1}$ mbar; (xxiii) $10^{-3}$ to $10^{-2}$ mbar; (xxiv) $10^{-4}$ to $10^{-3}$ mbar; and (xxv) $10^{-5}$ to $10^{-4}$ mbar.

The photons preferably have a wavelength in the range <100 nm, 100-200 nm, 200-300 nm, 300-400 nm, 400-500 nm, 500-600 nm, 600-700 nm, 700-800 nm, 800-900 nm, 900-1000 nm, 1-2 μm, 2-3 μm, 3-4 μm, 4-5 μm, 5-6 μm, 6-7 μm, 7-8 μm, 8-9 μm, 9-10 μm, 10-11 μm and >11 μm.

The method preferably further comprises transferring ions radially from the first ion guide section into the second ion guide section by urging ions across the pseudo-potential barrier.

The method preferably further comprises transferring ions radially from the second ion guide section into the first ion guide section by urging ions across the pseudo-potential barrier.

The method preferably further comprises providing a first mirror arranged at a first end of the ion guide and a second mirror arranged at a second end of the ion guide, the first and second mirrors forming an optical resonant cavity within the ion guide.

The first mirror and the second mirror preferably form either: (i) a plane-parallel resonant cavity; (ii) a concentric or spherical resonant cavity; (iii) a confocal resonant cavity; (iv) a hemispherical resonant cavity; or (v) a concave-convex resonant cavity.

The optical resonant cavity preferably comprises a stable resonator.

The optical resonant cavity preferably comprises an unstable resonator.

The laser beam preferably undergoes multiple reflections within the optical resonant cavity.

According to an aspect of the present invention there is provided a method of mass spectrometry comprising a method as described above.

According to an aspect of the present invention there is provided a mass spectrometer comprising:

a conjoined ion guide or ion trap comprising: (i) a first ion guide section comprising a plurality of electrodes each having an aperture through which ions are transmitted and wherein a first ion guiding path is formed within the first ion guide section; and (ii) a second ion guide section comprising a plurality of electrodes each having an aperture through which ions are transmitted and wherein a second ion guiding path is formed within the second ion guide section, wherein a radial pseudo-potential barrier is formed, in use, between the first ion guiding path and the second ion guiding path; and a device arranged and adapted to direct a laser beam along at least part of the axial length of the first ion guide section and/or the second ion guide section.

The device is preferably arranged and adapted to subject the ions to photo-dissociation.

The device is preferably arranged and adapted to cause cleavage of one or more disulfide bonds of ions.

The device is preferably arranged and adapted to subject the ions to photo-activation.

The device is preferably arranged and adapted to cause unfolding of ions or a change in conformation of ions.

The device is preferably arranged and adapted to perform ion spectroscopy.

The mass spectrometer preferably further comprises:
a laser which emits, in use, the laser beam comprising first photons; and
a device for scanning or varying the frequency of the first photons.

The mass spectrometer preferably further comprises a detector for detecting the first photons and/or a detector for detecting second photons emitted, in use, by ions.

The mass spectrometer preferably further comprises a Time of Flight mass analyser.

The mass spectrometer preferably further comprises a device for temporally separating ions according to their ion mobility.

The device for temporally separating ions according to their ion mobility is preferably located upstream and/or downstream of the ion guide or ion trap.

Ions are preferably confined radially and/or axially, in use, within the ion guide or ion trap.

The mass spectrometer preferably further comprises a control system arranged and adapted to generate one or more absorption spectra.

The mass spectrometer preferably further comprises a control system arranged and adapted to generate one or more emission spectra.

The mass spectrometer preferably further comprises a control system arranged and adapted to determine one or more properties of the ions from detecting the first photons and/or the second photons.

The mass spectrometer preferably further comprises a device arranged and adapted to maintain the ion guide or ion trap at a pressure selected from the group consisting of: (i) >100 mbar; (ii) >10 mbar; (iii) >1 mbar; (iv) >0.1 mbar; (v) >$10^{-2}$ mbar; (vi) >$10^{-3}$ mbar; (vii) >$10^{-4}$ mbar; (viii) >$10^{-5}$ mbar; (ix) >$10^{-6}$ mbar; (x) <100 mbar; (xi) <10 mbar; (xii) <1 mbar; (xiii) <0.1 mbar; (xiv) <$10^{-2}$ mbar; (xv) <$10^{-3}$ mbar; (xvi) <$10^{-4}$ mbar; (xvii) <$10^{-5}$ mbar; (xviii) <$10^{-3}$ mbar; (xix) 10-100 mbar; (xx) 1-10 mbar; (xxi) 0.1-1 mbar; (xxii) $10^{-2}$ to $10^{-1}$ mbar; (xxiii) $10^{-3}$ to $10^{-2}$ mbar; (xxiv) $10^{-4}$ to $10^{-3}$ mbar; and (xxv) $10^{-5}$ to $10^{-4}$ mbar.

The mass spectrometer preferably further comprises a laser arranged and adapted to emit the laser beam, wherein the laser beam comprises photons having a wavelength in the range <100 nm, 100-200 nm, 200-300 nm, 300-400 nm, 400-500 nm, 500-600 nm, 600-700 nm, 700-800 nm, 800-900 nm, 900-1000 nm, 1-2 μm, 2-3 μm, 3-4 μm, 4-5 μm, 5-6 μm, 6-7 μm, 7-8 μm, 8-9 μm, 9-10 μm, 10-11 μm and >11 μm.

The mass spectrometer preferably further comprises a device for transferring ions radially from the first ion guide section into the second ion guide section by urging ions across the pseudo-potential barrier.

The mass spectrometer preferably further comprises a device for transferring ions radially from the second ion guide section into the first ion guide section by urging ions across the pseudo-potential barrier.

The mass spectrometer preferably further comprises a first mirror arranged at a first end of the ion guide or ion trap and a second mirror arranged at a second end of the ion guide or ion trap, the first and second mirrors forming an optical resonant cavity within the ion guide or ion trap.

The first mirror and the second mirror form either: (i) a plane-parallel resonant cavity; (ii) a concentric or spherical resonant cavity; (iii) a confocal resonant cavity; (iv) a hemispherical resonant cavity; or (v) a concave-convex resonant cavity.

The optical resonant cavity preferably comprises a stable resonator.

The optical resonant cavity preferably comprises an unstable resonator.

The laser beam preferably undergoes multiple reflections within the optical resonant cavity.

According to another aspect of the present invention there is provided an ion guide or ion trap comprising:
a first mirror arranged at a first end of the ion guide and a second mirror arranged at a second end of the ion guide, the first and second mirrors forming an optical resonant cavity along a longitudinal axis of the ion guide.

The ion guide or ion trap is preferably selected from the group comprising:
(a) an ion tunnel ion guide comprising a plurality of electrodes, each electrode comprising one or more apertures through which ions are transmitted in use;
(b) an ion funnel ion guide comprising a plurality of electrodes, each electrode comprising one or more apertures through which ions are transmitted in use and wherein a width or diameter of an ion guiding region formed within the ion funnel ion guide increases or decreases along the axial length of the ion guide;
(c) a conjoined ion guide comprising: (i) a first ion guide section comprising a plurality of electrodes each having an aperture through which ions are transmitted and wherein a first ion guiding path is formed within the first ion guide section; and (ii) a second ion guide section comprising a plurality of electrodes each having an aperture through which ions are transmitted and wherein a second ion guiding path is formed within the second ion guide section, wherein a radial pseudo-potential barrier is formed between the first ion guiding path and the second ion guiding path;
(d) a multipole or segmented multipole rod set; or
(e) a planar ion guide comprising a plurality of planar electrodes arranged parallel to or orthogonal to a longitudinal axis of the ion guide.

The ion guide or ion trap preferably further comprises a device arranged and adapted to direct ions into and/or out of the ion guide or ion trap.

The first mirror and the second mirror preferably form either: (i) a plane-parallel resonant cavity; (ii) a concentric or spherical resonant cavity; (iii) a confocal resonant cavity; (iv) a hemispherical resonant cavity; or (v) a concave-convex resonant cavity.

The optical resonant cavity preferably comprises a stable resonator.

The optical resonant cavity preferably comprises an unstable resonator.

The laser beam preferably undergoes, in use, multiple reflections within the optical resonant cavity.

The optical path of the laser beam is preferably substantially co-axial with the axial length of the ion guide or ion trap and/or the path of ions within the ion guide or ion trap.

The laser beam preferably comprises photons having a wavelength in the range <100 nm, 100-200 nm, 200-300 nm, 300-400 nm, 400-500 nm, 500-600 nm, 600-700 nm, 700-800 nm, 800-900 nm, 900-1000 nm, 1-2 μm, 2-3 μm, 3-4 μm, 4-5 μm, 5-6 μm, 6-7 μm, 7-8 μm, 8-9 μm, 9-10 μm, 10-11 μm and >11 μm.

According to an aspect of the present invention there is provided a photo-dissociation device comprising an ion guide or ion trap as described above.

According to an aspect of the present invention there is provided a photo-activation device comprising an ion guide or ion trap as described above.

According to an aspect of the present invention there is provided an ion spectroscopy device comprising an on guide or ion trap as described above.

According to an aspect of the present invention there is provided a mass spectrometer comprising:
an ion guide or ion trap as described above; or
a photo-dissociation device as described above; or
a photo-activation device as described above; or
an ion spectroscopy device as described above.

The mass spectrometer preferably further comprises a Time of Flight mass analyser.

According to an aspect of the present invention there is provided a method comprising:
providing an ion guide or ion trap;
providing a first mirror arranged at a first end of the ion guide and a second mirror arranged at a second end of the ion guide, wherein the first and second mirrors form an optical resonant cavity along a longitudinal axis of the ion guide.

The ion guide or ion trap is preferably selected from the group comprising:
(a) an ion tunnel ion guide comprising a plurality of electrodes, each electrode comprising one or more apertures through which ions are transmitted in use;
(b) an ion funnel ion guide comprising a plurality of electrodes, each electrode comprising one or more apertures through which ions are transmitted in use and wherein a width or diameter of an ion guiding region formed within the ion funnel ion guide increases or decreases along the axial length of the ion guide;
(c) a conjoined ion guide comprising: (i) a first ion guide section comprising a plurality of electrodes each having an aperture through which ions are transmitted and wherein a first ion guiding path is formed within the first ion guide section; and (ii) a second ion guide section comprising a plurality of electrodes each having an aperture through which ions are transmitted and wherein a second ion guiding path is formed within the second ion guide section, wherein a radial pseudo-potential barrier is formed between the first ion guiding path and the second ion guiding path;
(d) a multipole or segmented multipole rod set; or
(e) a planar ion guide comprising a plurality of planar electrodes arranged parallel to or orthogonal to a longitudinal axis of the ion guide.

The method preferably further comprises directing ions into and/or out of the ion guide or ion trap.

The first mirror and the second mirror preferably form either: (i) a plane-parallel resonant cavity; (ii) a concentric or spherical resonant cavity; (iii) a confocal resonant cavity; (iv) a hemispherical resonant cavity; or (v) a concave-convex resonant cavity.

The optical resonant cavity preferably comprises a stable resonator.

The optical resonant cavity preferably comprises an unstable resonator.

The laser beam preferably undergoes multiple reflections within the optical resonant cavity.

The optical path of the laser beam is preferably substantially co-axial with the axial length of the ion guide or ion trap and/or the path of ions within the ion guide or ion trap.

The laser beam preferably comprises photons having a wavelength in the range <100 nm, 100-200 nm, 200-300 nm, 300-400 nm, 400-500 nm, 500-600 nm, 600-700 nm, 700-800 nm, 800-900 nm, 900-1000 nm, 1-2 µm, 2-3 µm, 3-4 µm, 4-5 µm, 5-6 µm, 6-7 µm, 7-8 µm, 8-9 µm, 9-10 µm, 10-11 µm and >11 µm.

According to an aspect of the present invention there is provided a method of photo-dissociation comprising a method as described above.

According to an aspect of the present invention there is provided a method of photo-activation comprising a method as described above.

According to an aspect of the present invention there is provided a method of ion spectroscopy comprising a method as described above.

According to an aspect of the present invention there is provided a method of mass spectrometry comprising:
a method as described above; or
a method of photo-dissociation as described above; or
a method of photo-activation as described above; or
a method of ion spectroscopy as described above.

The method preferably further comprises using a Time of Flight mass analyser to mass analyse ions.

According to an aspect of the present invention there is provided a method of mass spectrometry comprising:
using a control system to automatically and repeatedly switch a mass spectrometer during the course of a single experimental acquisition between a first mode of operation wherein parent ions are subjected to photo-dissociation to form first ions and a second mode of operation wherein parent ions are not subjected to photo-dissociation or are subjected to photo-dissociation to a lesser degree;
fragmenting at least some of the first ions into a plurality of fragment ions; and
mass analysing at least some of the plurality of fragment ions.

According to the above aspect of the present invention two main embodiments are contemplated. According to a first main embodiment a photo-dissociation source such as a UV laser may be repeatedly switched ON and OFF so as to cause photo-dissociation in one mode of operation and so that parent ions are not dissociated in the other mode of operation. According to a second main embodiment a photo-dissociation source may be left ON. In the first mode of operation ions are directed through the photo-dissociation region but in the second mode operation ions are caused to by-pass the photo-dissociation region.

The method preferably further comprises separating or filtering the parent ions and/or the first ions prior to the step of fragmenting at least some of the first ions.

The step of separating or filtering the parent ions and/or the first ions preferably comprises either:
(i) mass filtering the parent ions and/or the first ions; and/or
(ii) separating the parent ions and/or the first ions according to their ion mobility; and/or
(iii) separating the parent ions and/or the first ions according to their differential ion mobility.

Preferably, at least some of the parent ions comprise peptide complexes linked by one or more disulfide bonds and wherein in the first mode of operation at least some of the peptide complexes are caused to dissociate into a plurality of peptide sequences and/or a plurality of less complex peptide complexes.

The method preferably further comprises determining whether or not at least some of the parent ions comprise peptide complexes having one or more disulfide bonds.

The step of determining whether or not the parent ions comprise peptide complexes having one or more disulfide bonds preferably comprises determining whether the intensity of parent ions which are not subjected to photo-dissociation or are subjected to photo-dissociation to a lesser degree is substantially different from the intensity of the first ions.

The method preferably further comprises ionising ions eluting from a Liquid Chromatography source.

In the first mode of operation parent ions are preferably subjected to photo-dissociation by interacting the parent ions with a laser beam.

The laser beam preferably comprises an ultraviolet laser beam.

The laser beam preferably has a wavelength of 266 nm or a wavelength in the range 250-280 nm.

According to an aspect of the present invention there is provided a mass spectrometer comprising:

a control system arranged and adapted to automatically and repeatedly switch the mass spectrometer during the course of a single experimental acquisition between a first mode of operation wherein parent ions are subjected to photo-dissociation to form first ions and a second mode of operation wherein parent ions are not subjected to photo-dissociation or are subjected to photo-dissociation to a lesser degree;

a device arranged and adapted to fragment at least some of the first ions into a plurality of fragment ions; and a mass analyser arranged and adapted to mass analyse at least some of the plurality of fragment ions.

According to an aspect of the present invention there is provided a method of mass spectrometry comprising:

exposing protein or polypeptide ions to a photo-dissociation source operated in a first mode of operation to form first ions;

mass analysing the first ions and/or ions derived from the first ions to generate first mass spectral data;

exposing the protein or polypeptide ions to a photo-dissociation source operated in a second different mode of operation to form second ions;

mass analysing ions the second ions and/or ions derived from the second ions to generate second mass spectral data;

determining structural information related to the protein or polypeptide based upon the first mass spectral data and/or the second mass spectral data.

The photo-dissociation source preferably comprises a laser beam.

The laser beam preferably comprises an ultraviolet laser beam.

The laser beam preferably has a wavelength of 266 nm or a wavelength in the range 250-280 nm.

In the first mode of operation ions are preferably exposed to the laser beam for a first period of time and wherein in the second mode of operation ions are exposed to the laser beam for a second different period of time.

In the first mode of operation ions are preferably exposed to the laser beam having a first intensity and wherein in the second mode of operation ions are exposed to the laser beam having a second different intensity.

In the first mode of operation ions are preferably exposed to the laser beam having a first wavelength and wherein in the second mode of operation ions are exposed to the laser beam having a second wavelength.

According to an aspect of the present invention there is provided a mass spectrometer comprising:

a photo-dissociation source;

a control system arranged and adapted:

(i) to expose protein or polypeptide ions to the photo-dissociation source when operated in a first mode of operation to form first ions;

(ii) to mass analyse the first ions and/or ions derived from the first ions to generate first mass spectral data;

(iii) to expose the protein or polypeptide ions to the photo-dissociation source operated in a second different mode of operation to form second ions;

(iv) to mass analyse ions the second ions and/or ions derived from the second ions to generate second mass spectral data; and (v) to determine structural information related to the protein or polypeptide based upon the first mass spectral data and/or the second mass spectral data.

According to an aspect of the present invention there is provided a photo-dissociation device comprising:

an ion guide comprising a plurality of electrodes each having an aperture through which ions are transmitted in use;

a first mirror arranged at a first end of the ion guide and a second mirror arranged at a second end of the ion guide, the first and second mirrors forming an optical resonant cavity within the ion guide;

a device arranged and adapted to direct ions into and/or out of the ion guide; and a device arranged and adapted to direct a laser beam into the optical resonant cavity so that the laser beam undergoes, in use, multiple reflections within the optical resonant cavity and so that at least some ions within the ion guide are subjected to photo-dissociation.

The optical path of the laser beam is preferably substantially co-axial with the axial length of the ion guide and/or the path of ions within the ion guide.

The first mirror and the second mirror preferably form either: (i) a plane-parallel resonant cavity; (ii) a concentric or spherical resonant cavity; (iii) a confocal resonant cavity; (iv) a hemispherical resonant cavity; or (v) a concave-convex resonant cavity.

The optical resonant cavity preferably comprises a stable resonator.

The optical resonant cavity may alternatively comprise an unstable resonator.

According to an aspect of the present invention there is provided a mass spectrometer comprising a photo-dissociation device as described above.

The mass spectrometer preferably further comprises a fragmentation device arranged and adapted to fragment ions which have been subjected to photo-dissociation so as to form fragment ions.

The mass spectrometer preferably further comprises an Ion Mobility Spectrometer arranged and adapted to separate temporally ions which have been subjected to photo-dissociation and/or the fragment ions.

According to an aspect of the present invention there is provided a method of photo-dissociating ions comprising:

providing an ion guide comprising a plurality of electrodes each having an aperture through which ions are transmitted;

providing a first mirror arranged at a first end of the ion guide and a second mirror arranged at a second end of the ion guide, the first and second mirrors forming an optical resonant cavity within the ion guide;

directing ions into and/or out of the ion guide; and directing a laser beam into the optical resonant cavity so that the laser beam undergoes multiple reflections within the optical resonant cavity so that at least some ions within the ion guide are subjected to photo-dissociation.

According to an aspect of the present invention there is provided a mass spectrometer comprising:

a conjoined ion guide comprising: (i) a first ion guide section comprising a plurality of electrodes each having an aperture through which ions are transmitted in use and wherein a first ion guiding path is formed within the first ion guide section; and (ii) a second ion guide section comprising a plurality of electrodes each having an aperture through which ions are transmitted in use and wherein a second ion guiding path is formed within the second ion guide section, wherein a radial pseudo-potential barrier is formed between the first ion guiding path and the second ion guiding path;

a device arranged and adapted to direct a laser beam along at least part of the axial length of the second ion guide section so that, in use, at least some ions within the second ion guide section are subjected to photo-dissociation; and a device arranged and adapted either: (i) to transfer ions radially from the first ion guide section into the second ion guide section by urging ions across the pseudo-potential barrier; and/or (ii) to transfer ions radially from the second ion guide section into the first ion guide section by urging ions across the pseudo-potential barrier.

According to an aspect of the present invention there is provided a method of mass spectrometry comprising:

providing a conjoined ion guide comprising: (i) a first ion guide section comprising a plurality of electrodes each having an aperture through which ions are transmitted and wherein a first ion guiding path is formed within the first ion guide section; and (ii) a second ion guide section comprising a plurality of electrodes each having an aperture through which ions are transmitted and wherein a second ion guiding path is formed within the second ion guide section, wherein a radial pseudo-potential barrier is formed between the first ion guiding path and the second ion guiding path;

directing a laser beam along at least part of the axial length of the second ion guide section so that at least some ions within the second ion guide section are subjected to photo-dissociation; and either: (i) transferring ions radially from the first ion guide section into the second ion guide section by urging ions across the pseudo-potential barrier; and/or (ii) transferring ions radially from the second ion guide section into the first ion guide section by urging ions across the pseudo-potential barrier.

According to an aspect of the present invention there is provided a method of mass spectrometry comprising:

causing biomolecular ions to at least partially unfold to form first ions by either: (i) subjecting the biomolecular ions or ions derived from the biomolecular ions to IR photoactivation; and/or (ii) exposing the biomolecular ions or ions derived from the biomolecular ions to acidic vapours; and/or (iii) subjecting the biomolecular ions or ions derived from the biomolecular ions to UV photo-dissociation; and then fragmenting at least some of the first ions to form second ions.

The step of fragmenting at least some of the first ions preferably comprises fragmenting at least some of the first ions by Electron Transfer Dissociation and/or by UV photo-dissociation.

The method preferably further comprises:

separating at least some of the first ions temporally according to their ion mobility or differential ion mobility; and/or separating at least some of the second ions temporally according to their ion mobility or differential ion mobility.

According to an aspect of the present invention there is provided a mass spectrometer comprising:

a device arranged and adapted to cause biomolecular ions to at least partially unfold to form first ions by either: (i) subjecting the biomolecular ions or ions derived from the biomolecular ions to IR photoactivation; and/or (ii) exposing the biomolecular ions or ions derived from the biomolecular ions to acidic vapours; and/or (iii) subjecting the biomolecular ions or ions derived from the biomolecular ions to UV photo-dissociation; and a fragmentation device arranged and adapted to fragment at least some of the first ions to form second ions.

According to an aspect of the present invention there is provided a method of mass spectrometry comprising:

subjecting biomolecular ions to Hydrogen-Deuterium exchange; and then causing the biomolecular ions to at least partially unfold to form first ions by either (i) subjecting the biomolecular ions or ions derived from the biomolecular ions to IR photoactivation; and/or (ii) exposing the biomolecular ions or ions derived from the biomolecular ions to acidic vapours; and/or (iii) subjecting the biomolecular ions or ions derived from the biomolecular ions to UV photo-dissociation.

According to an aspect of the present invention there is provided a method of mass spectrometry comprising:

causing biomolecular ions to at least partially unfold to form first ions by either: (i) subjecting the biomolecular ions or ions derived from the biomolecular ions to IR photoactivation; and/or (ii) exposing the biomolecular ions or ions derived from the biomolecular ions to acidic vapours; and/or (iii) subjecting the biomolecular ions or ions derived from the biomolecular ions to UV photo-dissociation; and then subjecting the first ions to Hydrogen-Deuterium exchange.

The method preferably further comprises fragmenting at least some of the first ions to form second ions.

The step of fragmenting at least some of the first ions preferably comprises fragmenting at least some of the first ions by Electron Transfer Dissociation and/or by UV photo-dissociation.

The method preferably further comprises:

separating at least some of the first ions temporally according to their on mobility or differential ion mobility; and/or separating at least some of the second ions temporally according to their ion mobility or differential ion mobility According to an aspect of the present invention there is provided a mass spectrometer comprising:

a device arranged and adapted to subject biomolecular ions to Hydrogen-Deuterium exchange; and a device arranged and adapted to cause the biomolecular ions to at least partially unfold to form first ions by either: (i) subjecting the biomolecular ions or ions derived from the biomolecular ions to IR photoactivation; and/or (ii) exposing the biomolecular ions or ions derived from the biomolecular ions to acidic vapours; and/or (iii) subjecting the biomolecular ions or ions derived from the biomolecular ions to UV photo-dissociation.

According to an aspect of the present invention there is provided a mass spectrometer comprising:

a device arranged and adapted to cause biomolecular ions to at least partially unfold to form first ions by either: (i) subjecting the biomolecular ions or ions derived from the biomolecular ions to IR photoactivation; and/or (ii) exposing the biomolecular ions or ions derived from the biomolecular ions to acidic vapours; and/or (iii) subjecting the biomolecular ions or ions derived from the biomolecular ions to UV photo-dissociation; and a device arranged and adapted to subject the first ions to Hydrogen-Deuterium exchange.

According to a first aspect of the present invention there is provided a method and apparatus for performing High/Low photo-dissociation.

According to an embodiment a laser may be used in an LC/MS$^E$ style experiment in which spectra are alternately acquired with the laser switched ON (High) and switched OFF (Low). As the analyte precursor elutes from the LC system the reduction in intensity of the precursor signal in the "High" data along with the time-aligned appearance of the fragment peptide chains may be used to the presence of a disulfide linked peptide or peptide chains.

In a further embodiment, a subsequent secondary fragmentation method CID (or other fragmentation methods such as Electron Transfer Dissociation (ETD), Electron Capture Dissociation (ECD), Surface Induced Dissociation (SID) or further photo-fragmentation) may be used to obtain sequence information for the individual chains.

According to a second aspect of the present invention there is provided a method and apparatus for structural elucidation.

According to an embodiment a laser may be used to fragment intact proteins. According to this embodiment disulfide bonds located on the exterior of a protein will have the most exposure to the laser and will break first. Subsequent fragmentation (by any means) will yield products originating from the exterior surface of the protein.

According to an embodiment the degree of exposure to the laser may be controlled to provide a range of levels of fragmentation and therefore structural information, ideally by systematically dismantling a protein from the outside in.

According to an embodiment the preferred technique provides a degree of structural information analogous to hydrogen deuterium exchange (HDX) labelling or ETD/ECD experiments where the fragment ions observed are preferentially generated from the surface of the protein which is most exposed to the reagent or electrons.

This embodiment may be combined with ion mobility and/or ETD/CID fragmentation and/or HDX.

According to an embodiment the mass spectrometer preferably further comprises an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; and (xx) a Glow Discharge ("GD") ion source.

The mass spectrometer preferably further comprises one or more continuous or pulsed ion sources.

The mass spectrometer preferably further comprises one or more ion guides.

The mass spectrometer preferably further comprises one or more ion mobility separation devices and/or one or more Field Asymmetric Ion Mobility Spectrometer devices.

The mass spectrometer preferably further comprises one or more ion traps or one or more ion trapping regions.

The mass spectrometer preferably further comprises one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an on-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The mass spectrometer may comprise one or more energy analysers or electrostatic energy analysers.

The mass spectrometer preferably comprises one or more ion detectors.

The mass spectrometer preferably further comprises one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter.

The mass spectrometer preferably further comprises a device or ion gate for pulsing ions.

The mass spectrometer preferably further comprises a device for converting a substantially continuous ion beam into a pulsed ion beam.

The mass spectrometer may further comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

BRIEF DESCRIPTION OF THE DRAWINGS

Various embodiments of the present invention will now be described together with other arrangements given for illustrative purposes only, by way of example only, and with reference to the accompanying drawings in which:

FIG. 3A shows a known Surface Induced Dissociation ("SID") fragmentation cell and FIG. 3B shows an embodiment of the present invention wherein ions may be subjected to photo-dissociation in an ion guide and the resulting peptide ions may then be subjected to SID fragmentation in a modified SID fragmentation cell arranged downstream of the ion guide;

DETAILED DESCRIPTION OF THE PREFERRED EMBODIMENTS

Figure 1:
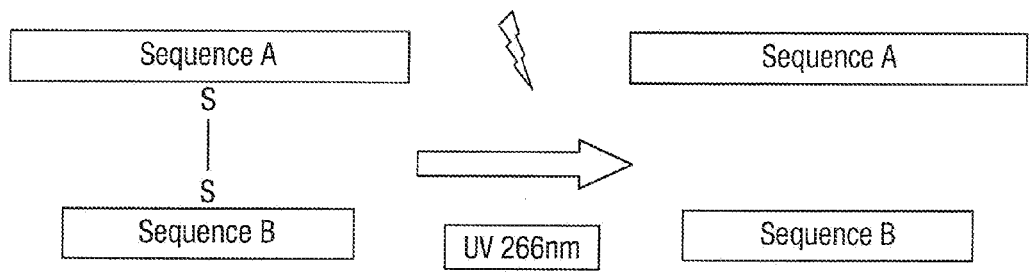
FIG. 1 illustrates a known process wherein a disulfide linked peptide complex is fragmented using a UV laser to yield separated peptide chains.

As has been discussed above, FIG. 1 shows a known arrangement wherein a UV YAG laser at a wavelength of 266 nm is used to preferentially cleave S—S bonds of peptide complex ions held in an ion trap. The laser beam from the YAG laser causes photo-dissociation of peptide complex ions A-B resulting in a separate peptide ion sequence ion A and a separate peptide ion sequence ion B. Both peptide ion sequence ions A,B can then be separately mass analysed and detected.

Figure 2:
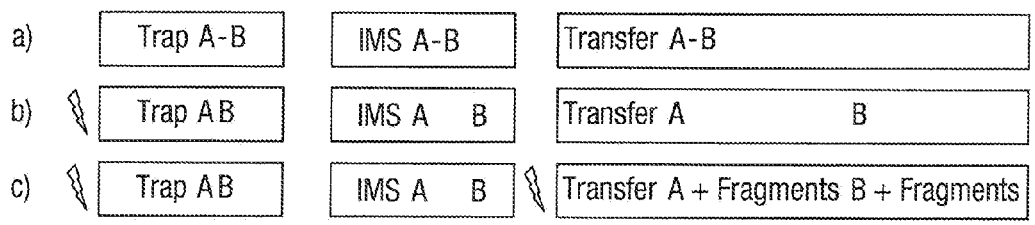
FIG. 2A shows an embodiment of the present invention wherein an intact precursor ion A-B is transmitted from an ion trap to an ion Mobility Spectrometer section and is then transmitted through an ion transfer section.
FIG. 2B shows an embodiment wherein a precursor ion A-B is photo-dissociated into peptide ions A and B in an ion trap and wherein the peptide ions A and B are then separated temporally as they are transmitted through an Ion Mobility Spectrometer section before the separate peptide ions A and B are transmitted through the ion transfer section and FIG. 2C shows an embodiment of the present invention wherein the precursor ion A-B is photo-dissociated into separate peptide ions A and B in an ion trap and wherein the separate peptide ions A and B are then separated temporally as they are transmitted through an Ion Mobility Spectrometer section and wherein the peptide ion A is then fragmented upon entering the ion transfer section and wherein the peptide ion B is fragmented at a subsequent time upon entering the ion transfer section.

FIG. 2A shows an embodiment of the present invention wherein an intact precursor ion A-B is transmitted from an ion trap into an Ion Mobility Spectrometer ("IMS") section. The precursor ions pass through the IMS section and are then passed on to an ion transfer section.

FIG. 2B shows an embodiment wherein a precursor ion A-B is photo-dissociated into separate peptide ions A and B within the on trap. The resulting peptide ions A,B are then passed on to the IMS section wherein the ions A,B become separated temporally as they are transmitted through the Ion Mobility Spectrometer section. The peptide ions A,B arrive at the exit of the IMS section at different times and the peptide ions A,B are then sequentially transmitted through the ion transfer section.

FIG. 2C shows an embodiment of the present invention wherein the precursor on A-B is photo-dissociated into separate peptide ions A,B in the ion trap. The separate peptide ions A,B are then separated temporally as they are transmitted through the Ion Mobility Spectrometer section. The peptide ion B emerges first from the IMS section and is then fragmented upon entering or within the ion transfer section. As a result, peptide ions B and corresponding fragment ions are preferably transmitted through the ion transfer section and are mass analysed. Peptide ions A arrive at the exit of the IMS section at a later time and are preferably also fragmented upon entering or within the ion transfer section. As a result, peptide ions A and corresponding fragment ions are preferably transmitted through the ion transfer section and are mass analysed.

According to the embodiment shown in FIG. 2C ion mobility separation of fragment peptide chain ions A,B prior to secondary fragmentation as ions enter or within the ion transfer section allows drift time alignment of product ions to precursor ions, producing clean time-aligned product ion spectra for each of the first generation fragment peptide chains.

The peptide complex ions may be photo-dissociated in an ion trap as described above. In an alternative embodiment, the source of ions preferably comprises a matrix-assisted laser desorption/ionisation (MALDI) source, wherein the laser intensity and/or wavelength is chosen to promote in-source photo-dissociation of the disulfide bonds. In another embodiment, the laser intensity and/or wavelength may be repeatedly switched between a normal mode and an in-source photo-fragmentation mode.

Fragmentation of the peptide ions may be achieved using any desired method. For example, using Collision Induced Dissociation ("CID"), Electron Transfer Dissociation ("ETD"), Surface Induced Dissociation ("SID"), or photo-fragmentation with a UV or IR laser beam or light source.

According to another embodiment of the present invention, an ion transfer section is provided downstream of an IMS section. Ions are arranged to be transmitted through the IMS section before being transmitted through the ion transfer section. A UV laser or light source is preferably provided to illuminate ions within the ion transfer section. According to a preferred embodiment, the laser or light source is activated at times corresponding to known drift times through the IMS section of selected ions. Accordingly, ions having a known drift time or drift time distribution through the IMS section are selectively illuminated, and preferably fragmented, within the ion transfer section.

According to this embodiment, fragment ions and non-fragmented ions are preferably transmitted through the ion transfer section using travelling waves in order to preserve their temporal separation. The laser or light source may be activated multiple times over the course of an IMS separation, or multiple times during the elution of a selected ion species.

The preferred embodiment also addresses the problem of introducing a laser beam or other light source into a mass spectrometer in order to cause photo-dissociation or fragmentation of ions. According to the preferred embodiment of the present invention ions may be held along the axis of a travelling wave device or ion guide. The travelling wave device or ion guide preferably comprises a plurality of electrodes each having an aperture through which ions are transmitted in use. One or more transient DC voltages or transient DC voltage waveforms are preferably applied to the electrodes forming the ion guide in order to urge ions along the axial length of the ion guide.

According to the preferred embodiment ions are held within the travelling wave device or ion guide and a laser beam or other light source is preferably directed and aligned along the axis of the travelling wave device or ion guide in order to cause maximum overlap of the light with the ion beam.

FIG. 3A shows a known arrangement wherein ions from a quadrupole are passed through entrance lenses and are deflected by entrance deflectors and a central deflector onto a Fluorinated Self-Assembled Monolayer ("F-SAM") surface where the ions are caused to fragment by Surface Induced Dissociation ("SID") upon impacting the surface. The resulting fragment ions are then directed by exit deflectors and exit lenses to a downstream collision cell.

Figure 3B:
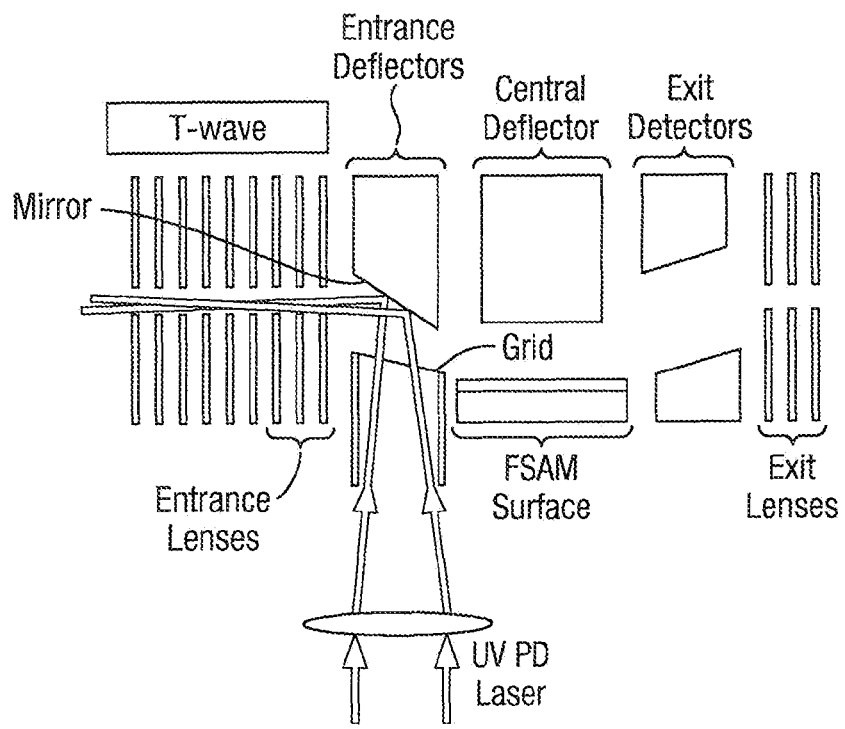

FIG. 3B shows an embodiment of the present invention wherein a modified SID fragmentation device is used. A laser beam from a UV laser source is focused by a lens through a grid electrode onto a mirror provided on an angled surface of an entrance deflector. The laser beam is directed by the mirror back along the central longitudinal axis of an ion guide. The ion guide preferably comprises a plurality of electrodes each having an aperture through which ions are transmitted in use. One or more transient DC voltages or transient DC voltage waveforms are preferably applied to the electrodes forming the ion guide in order to urge ions along the axial length of the ion guide. Parent ions are preferably confined along the axial length of the ion guide and the laser beam which is directed back along the axial length of the ion guide preferably overlaps with the ion confinement region within the ion guide. The laser beam preferably causes the parent ions to be subjected to photo-dissociation and complex peptide ions having disulfide bonds are preferably dissociated into a plurality of peptide ions.

Ions which have been subjected to photo-dissociation are preferably urged towards the exit of the ion guide by the application of the one or more transient DC voltages to the electrodes forming the ion guide. The ions are then directed by one or more entrance lenses and/or entrance deflectors and/or the grid electrode and/or a central deflector onto a F-SAM layer. The ions are preferably caused to fragment by Surface Induced Dissociation upon impacting the surface. The resultant fragment ions are then preferably deflected by exit deflectors and exit lenses to one or more downstream ion-optical components such as a collision cell and/or a mass analyser.

Other embodiments are contemplated wherein the laser beam or light source may also be used for photo-excitation or photo-activation of ions in the ion guide. For example, according to an embodiment the laser beam or light source may have a wavelength in the infrared ("IR") and may have a wavelength in the range 1-2 µm. The IR laser beam or light source may be used to at least partially unfold ions such as protein ions or polypeptide ions preferably without fragmenting the ions. A visible or IR laser or light source may be used to cause photoluminescence of ions.

Figure 4:
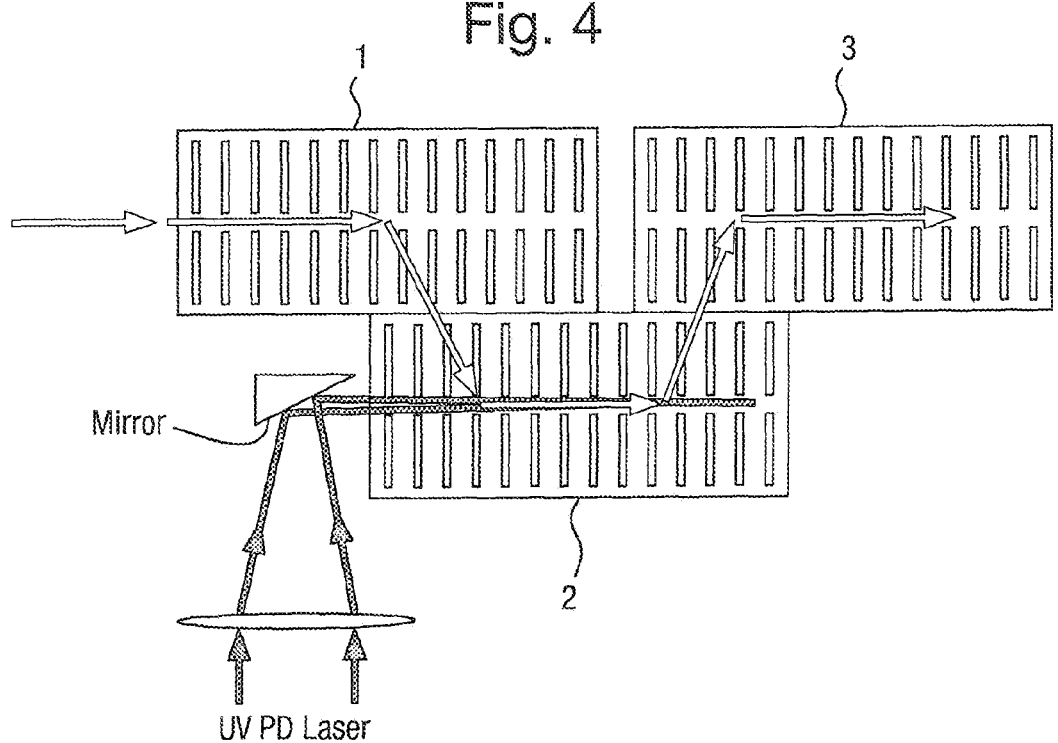
FIG. 4 shows an embodiment of the present invention wherein a conjoined ion guide is provided and wherein ions are diverted from a main ion guide section into a photo-dissociation ion guide section in which the ions are subjected to photo-dissociation before the ions are then diverted back into the main ion guide section.

According to another embodiment of the present invention an offset conjoined ion guide referred to as a "Stepwave" device may be used such as is disclosed in GB-2455171 (the entire contents of which are incorporated herein by reference). FIG. 4 shows schematically an embodiment of the present invention wherein an offset conjoined ion guide allows direct on-axis illumination of ions. According to this embodiment a first ion guide 1 is preferably provided having a plurality of ring electrodes. Adjacent ring electrodes are preferably maintained, in use, at opposite phases of an applied RF voltage. Ions are preferably confined radially within the first ion guide 1 by a radial pseudo-potential force.

A second ion guide 2 is preferably provided alongside or adjacent at least a portion of the first ion guide 1. A conjoined ion section is preferably provided where the first ion guide 1 and the second ion guide 2 overlap or are otherwise in close proximity with each other. Ions which enter the first ion guide 1 preferably continue into a conjoined ion guide section. The conjoined ion guide section preferably comprises ring electrodes which form part of the first ion guide 1 and also ring electrodes which preferably form part of a second ion guide 2. The ring electrodes in the conjoined ion guide section are preferably positioned side by side and preferably have aligned radial cut-out portions between the ring electrodes. As a result, ions may under the influence of a radial DC electric field be deflected within the conjoined ion guide section from the first ion guide 1 across a pseudo-potential barrier between the first ion guide 1 and the second ion guide 2 into the second ion guide 2. According to an embodiment ions are preferably trapped within the second ion guide 2.

Ions which are deflected within the conjoined ion guide section from the first ion guide 1 into the second ion guide 2 preferably continue to move along and within the conjoined ion guide section. According to an embodiment one or more transient DC voltages or transient DC voltage waveforms may be applied to the electrodes of the conjoined ion guide section in order to translate or urge ions along at least a part or substantially the whole of the axial length of the conjoined ion guide section.

The conjoined ion guide section preferably comprises ring electrodes which form part of the second ion guide 2 and ring electrodes which preferably form part of a third ion guide 3. The ring electrodes in the conjoined ion guide section are preferably positioned side by side with aligned radial cut-out portions between the ring electrodes. As a result, ions may under the influence of a radial DC electric field be deflected within the conjoined ion guide section from the second ion guide 2 across a pseudo-potential barrier between the second ion guide 2 and the third ion guide 3 into the third ion guide 3.

The third ion guide 3 may comprise an Ion Mobility Spectrometry ("IMS") section. According to an embodiment the third ion guide 3 may be co-axial with the first ion guide 1. According to an embodiment the first ion guide 1 and the third ion guide 3 may form a substantially continuous on guide.

According to an embodiment of the present invention a control system may be arranged to repeatedly and alternately switch between a first mode wherein ions continue from the first ion guide direct into the third ion guide 3 and a second mode wherein ions are diverted from the first ion guide 1 into the second ion guide 2 before being diverted back into the third ion guide 3.

According to the preferred embodiment ions are diverted away from and back along the main optical axis of the instrument (which is preferably co-axial with the longitudinal axis of the first ion guide 1 and/or the third ion guide 3) using DC electric fields.

In a mode of operation ions may be trapped in an ion trap section which is preferably formed within the second ion guide 2 and may be subjected to photo-dissociation using an ultraviolet ("UV") laser beam. The resulting fragment ions may then be transferred from the second ion guide 2 into the third ion guide 3.

According to this embodiment, the laser beam may remain ON while the control system repeatedly and alternately switches between the first mode wherein ions continue from the first ion guide directly into the third ion guide 3 and the second mode wherein ions are diverted from the first ion guide 1 into the second ion guide 2 before being diverted back into the third ion guide 3 so that ions are repeatedly switched between a first mode of operation wherein the ions are subjected to photo-dissociation and a second mode of operation wherein the ions are not substantially subjected to photo-dissociation.

According to another embodiment of the present invention the laser beam which preferably traverses at least a portion of the axial length of the second ion guide 2 may be repeatedly switched ON and OFF so that ions diverted into the second ion guide 2 are repeatedly switched between a first mode of operation wherein the ions are subjected to photo-dissociation and a second mode of operation wherein the ions are not substantially subjected to photo-dissociation.

According to other embodiments other types of laser or other light sources may alternatively or additionally be used. For example, an infrared ("IR") laser may be used in a $MS^E$ experiment to help "unfold" proteins or peptides rendering them more amenable to fragmentation such as UV photo-dissociation as described above or by Electron Transfer Dissociation ("ETD") or by other means. A light source such as a vacuum ultra-violet lamp may be used to cause photo-dissociation of ions. According to an embodiment, the laser or light source used to cause photo-dissociation of ions preferably has a wavelength in the range of 100 nm to 300 nm. These wavelengths can be generated by suitable lamps or lasers.

With reference to FIGS. 2A-2C an instrument or mass spectrometer may cycle among and between one or more different modes of operation or acquisition many times during the elution of a chromatographic peak. First generation fragments ions A,B may according to an embodiment of the present invention be associated with parent or precursor ions A-B based on retention time. Second generation fragment ions can also be associated with first generation fragments based on retention time and drift time.

The analysis of more compact folded proteins (or those sprayed via "native" ESI buffer conditions) by ETD can be challenging because the folded proteins may have limited charges exposed for the ETD ion-ion reaction and limited charge state distributions for precursor choice. According to an embodiment of the present invention protein ions may be trapped within an ion trap. The ion trap may, for example, comprise a TWAVE cell comprising a plurality of electrodes each having an aperture through which ions are transmitted in use and wherein one or more transient DC voltages may be applied to the electrodes in order to urge ions along the axial length of the ion trap. According to this embodiment the protein ions may be unfolded or at least partially unfolded and/or at least partially fragmented via either: (i) cleavage of some or all disulphide bonds using a UV laser beam from a UV laser; and/or (ii) coulombic repulsion as the charge state is increased by admitting acidic vapours into the ion trap or cell; and/or (iii) IR laser activation to at least partially unfold the protein ions preferably without causing the protein ions to fragment.

A particularly advantageous feature of this embodiment is that the at least partially unfolded protein ions and/or disulphide cleaved fragment ions are more amenable to ETD fragmentation. The at least partially unfolded protein ions and/or disulphide cleaved fragment ions may be subjected to ETD fragmentation either in the same ion trap cell in which the protein ions were unfolded and/or subjected to UV photo-dissociation or alternatively the protein ions may be subjected to ETD fragmentation in a downstream ion trap or cell. The unfolding of the proteins coupled with UV photo-dissociation is particularly advantageous in that the resulting analyte ions have more charges exposed, are more unfolded and are more amenable to subsequent analysis by, for example, ETD fragmentation.

According to an embodiment first generation product ions may be separated temporally by ion mobility separation prior to being subjected to ETD fragmentation. Additionally or alternatively, second generation ETD product ions may be separated temporally according to their ion mobility.

According to another embodiment of the present invention protein ions may be subjected to Hydrogen-Deuterium Exchange ("HDX" or "HDx") enhancement where the location of the Hydrogen-Deuterium exchange sites are determined for folded and native proteins/peptides. According to this embodiment protein ions may be unfolded within an ion trap. The ion trap may, for example, comprise a TWAVE cell comprising a plurality of electrodes each having an aperture through which ions are transmitted in use and wherein one or more transient DC voltages may be applied to the electrodes in order to urge ions along the axial length of the ion trap. The protein ions may be at least partially unfolded via either: (i) cleavage of some or all the disulphide bonds using a UV laser beam from a UV laser; and/or (ii) coulombic repulsion as the charge state is increased by admitting acidic vapours admitted into the ion trap or cell; and/or (iii) IR laser activation to at least partially unfold the protein ions preferably without causing the protein ions to fragment.

A particular advantage of this embodiment this that HDX labelled sites are not scrambled. Following the at least partial unfolding of protein ions according to this embodiment, the protein ions may then be subjected to ETD analysis to identify the sites of Hydrogen-Deuterium labelling (as ETD has a significantly lower scrambling effect than CID) or alternatively the protein ions may be subjected to UV photofragmentation. First generation product ions may be temporally separated according to their ion mobility before being subjected to ETD fragmentation. Alternatively, second generation ETD product ions may be temporally separated by passing the product ions through an ion mobility separator or spectrometer.

According to another embodiment, parent ions may be subjected to modification with chromophores or UV-tags, such as known UV absorbing dyes and/or compounds engineered to absorb specific frequencies of light. For example, a chromophore may be engineered to attach to a particular site on an ion. Preferably, this allows additional control over the fragmentation process of the ion.

Figure 5:
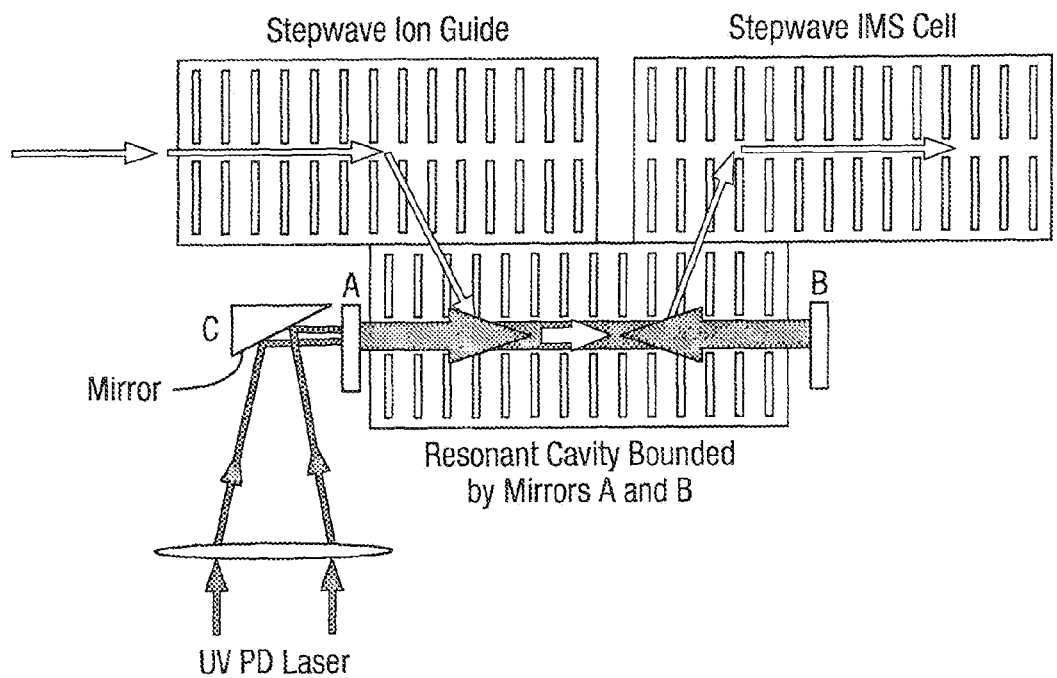
FIG. 5 shows an embodiment of the present invention wherein a laser beam from a UV laser source forms a resonant cavity within an ion guide bounded by two mirrors.

For photofragmentation, the overlap of analyte ions and a laser beam or other light source can be significantly enhanced or otherwise optimised by arranging a stepwave device or conjoined ion guide to act as an optical resonant cavity. An embodiment of the present invention is shown in FIG. 5. With reference to FIG. 5, an ion guide is preferably provided. According to the preferred embodiment the ion guide comprises a TWAVE ion guide comprising a plurality of electrodes each having an aperture through which ions are transmitted in use and wherein one or more transient DC voltages may be applied to the electrodes in order to urge ions along the axial length of the ion guide. However, according to other less preferred embodiments the ion guide may include a multipole rod set ion guide or an arrangement comprising a plurality of planar electrodes arranged substantially in the plane of ion travel for at least a portion of the length of the ion guide.

According to the preferred embodiment mirrors A,B are provided at each end of the ion guide device so that laser light once incident within the ion guide is preferably reflected back and forth between the mirrors multiple times. As a result, according to a preferred embodiment of the present invention a resonant cavity is preferably provided within the ion guide. The geometry (resonator type) may be chosen so that the light beam remains stable i.e. the size of the beam does not continually grow with multiple reflections. According to this embodiment a stable resonator may be provided by using an aperture or partially reflecting mirror in order to inject the light into the cavity and the decay of the light within the cavity is preferably determined by the aperture size and/or reflectivity of the mirrors A,B.

The two mirrors A,B have radii R1,R2 and are separated by length L. According to various embodiments of the present invention the mirrors A,B may be either concentric spherical, confocal, hemispherical, concave-convex or plane parallel arrangements. Mirror C is not part of the optical resonator but is preferably provided to reflect a laser beam emitted from a laser source into and along the axis of the ion guide.

Figure 6:
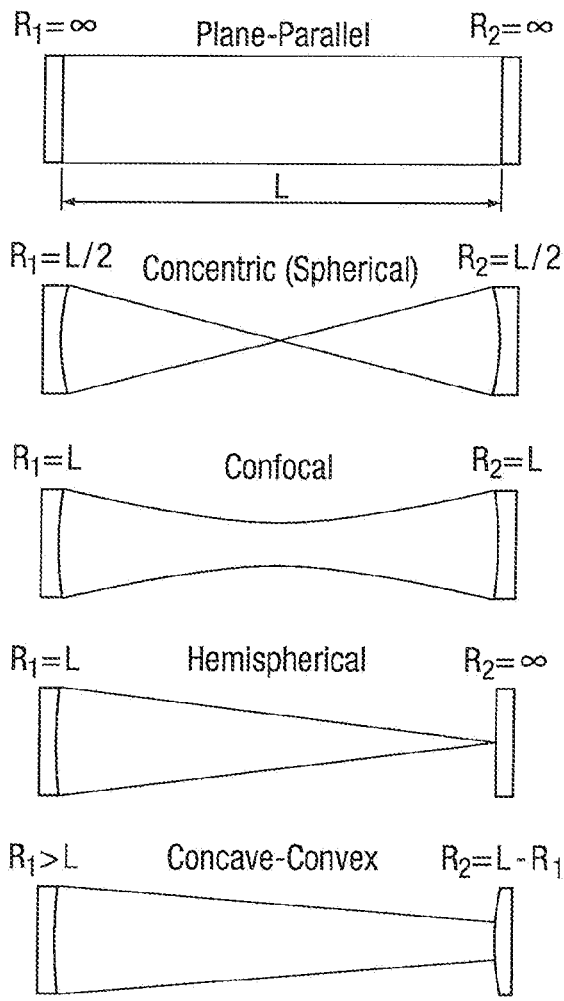
FIG. 6 shows different examples of stable resonator configurations which may be employed according to embodiments of the present invention.

FIG. 6 shows different examples of stable resonator configurations which may be employed according to embodiments of the present invention.

Figure 7:
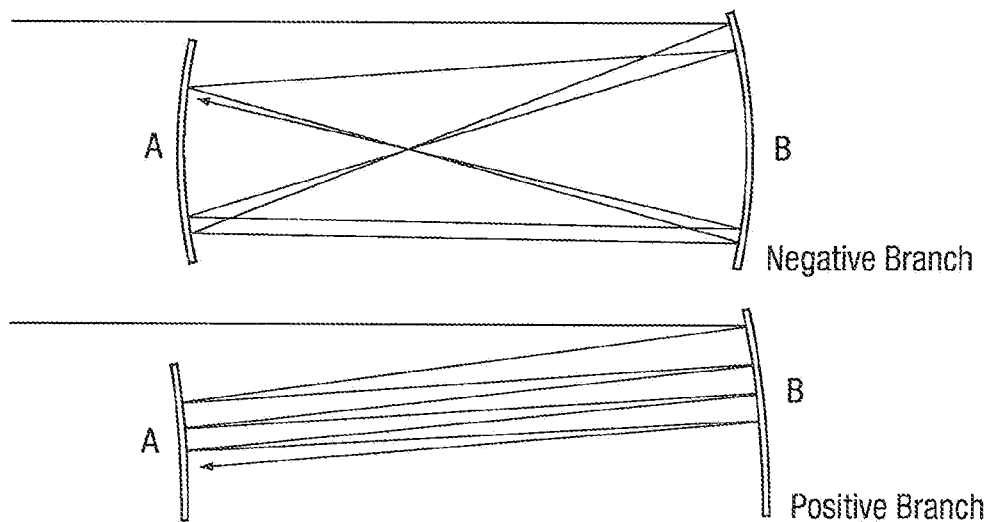
FIG. 7 shows examples of unstable resonator configurations which may be employed according to other less preferred embodiments of the present invention.

According to an alternative embodiment the resonator type may be arranged to be unstable so that the laser light is injected into the resonant cavity past the edge of, for example, mirror A. According to this embodiment the light preferably undergoes multiple passes within the resonator cavity but preferably without repeating its path and at the same time gradually becoming more confined. FIG. 7 shows examples of unstable resonator configurations which may be employed according to other embodiments of the present invention. As shown in FIG. 7, the unstable resonator may comprise either a positive or negative branch resonator type.

According to another embodiment of the present invention, the laser beam or light source is not aligned along the axis of the ion guide, but is instead arranged to intersect the ion beam at an angle. For example, the laser beam or light source may be arranged to orthogonally intersect the ion beam. According to a preferred embodiment, ions are held along the axis of a travelling wave device or ion guide which comprises a plurality of electrodes each having an aperture through which ions are transmitted in use. A laser beam or light source is preferably arranged so that the light passes between the electrodes of the travelling wave device or ion guide.

Figure 8:
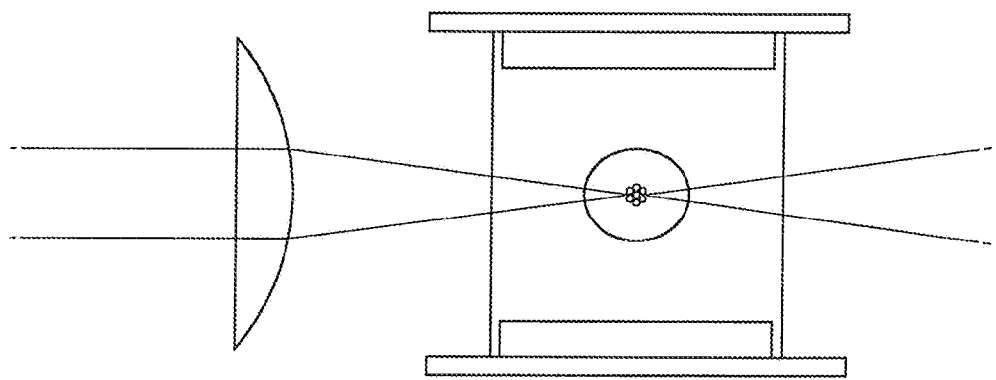
FIG. 8 shows an embodiment of the present invention wherein a laser beam or light source is arranged to orthogonally intersect an ion beam as it is held along the axis of an ion guide.

According to an embodiment, focussing elements are provided in order to focus the light FIG. 8 shows an embodiment according to which a laser beam or light source is arranged to orthogonally intersect an ion beam as it is held along the axis of an ion guide. A lens is provided to focus the laser beam or light source to a point along the ion beam. The light passes between two electrodes (only one electrode is shown) of the ion guide.

Figure 9A:
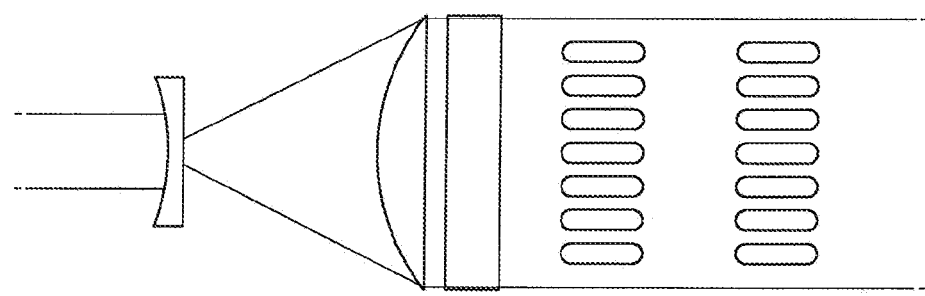
FIGS. 9A and 9B show an embodiment of the present invention wherein lenses including cylindrical lenses are provided in order to focus light from a laser or light source into a line along the axis of an ion guide.
Figure 9B:
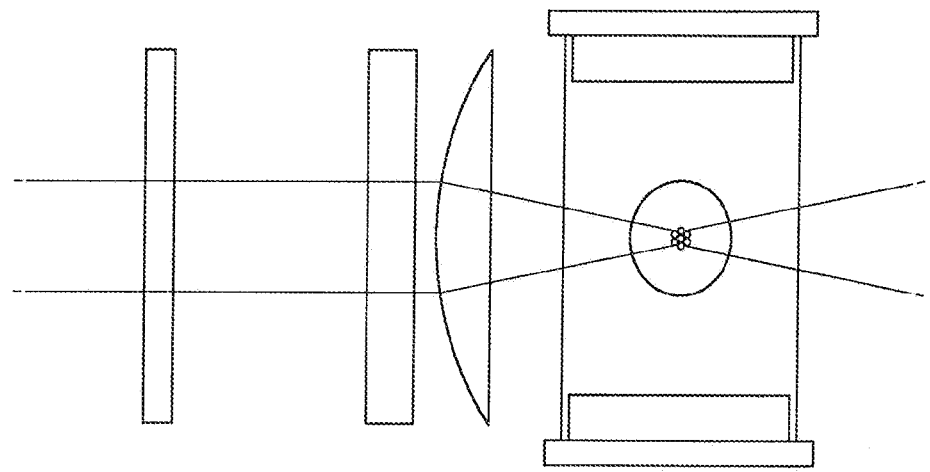

According to another embodiment, a cylindrical lens is provided. Preferably, the cylindrical lens is arranged to focus the light into a line along the axis of the ion guide. FIGS. 9A and 9B show an embodiment wherein a cylindrical lens is provided in order to focus light from the laser or light source into a line along the axis of the ion guide.

Figure 10:
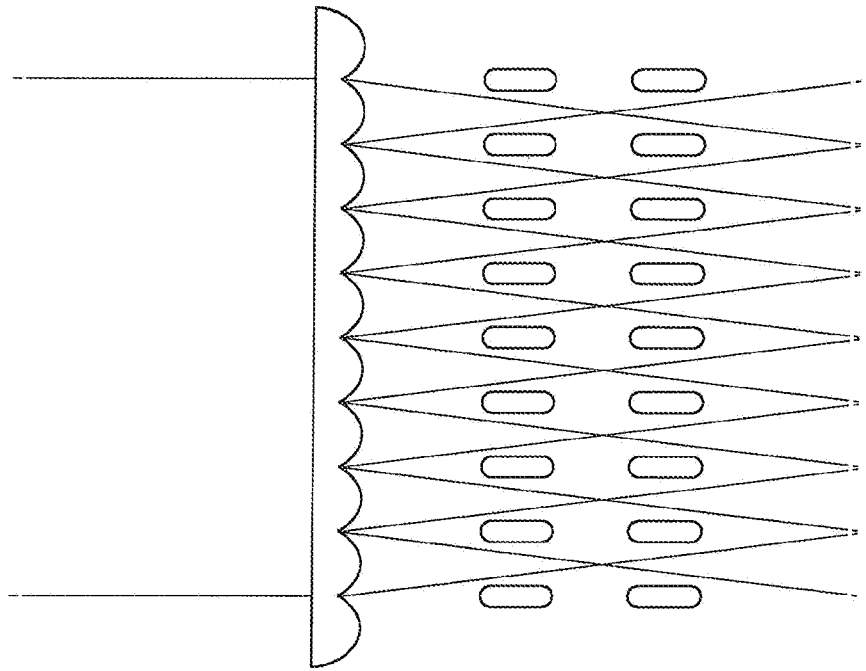
FIG. 10 shows an embodiment of the present invention wherein a multiple focussing array element is used to focus light at multiple points along the axis of an ion guide.

FIG. 10 shows another embodiment of the present invention in which a multiple focussing array element, such as a lenticular lens, is used to focus the light from a laser or a light source at multiple points along the axis of an ion guide. The multiple focussing array element is preferably arranged such that the light passes in between the electrodes of the ion guide.

According to these embodiments, one or more mirrors may be provided adjacent to the travelling wave device or ion guide so that light which intersects the ion beam once is preferably reflected back through the ion guide and intersects the ion beam again. Preferably, multiple mirrors are provided so that the light is reflected back and forth between the mirrors and intersects the ion beam multiple times. As a result, the total photon flux at the ion beam is preferably increased.

According to another embodiment of the present invention, a light detector is provided. Preferably, the light detector is provided adjacent to the travelling wave device or ion guide. The light detector may comprise, for example, a CCD array. According to the preferred embodiment, the light detector is used to measure luminescence from ions. For example, the light detector may be used to measure photoluminescence such as fluorescence from ions which have been exposed to light from the laser or light source. These ions may or may not have been photo-fragmented. According to this embodiment, the light detector is preferably positioned such that it does not receive light directly from the laser or light source.

A spectrometer is preferably provided in combination with the light detector. The spectrometer is preferably arranged to facilitate spectrographic measurements of the luminescence.

Figure 11:
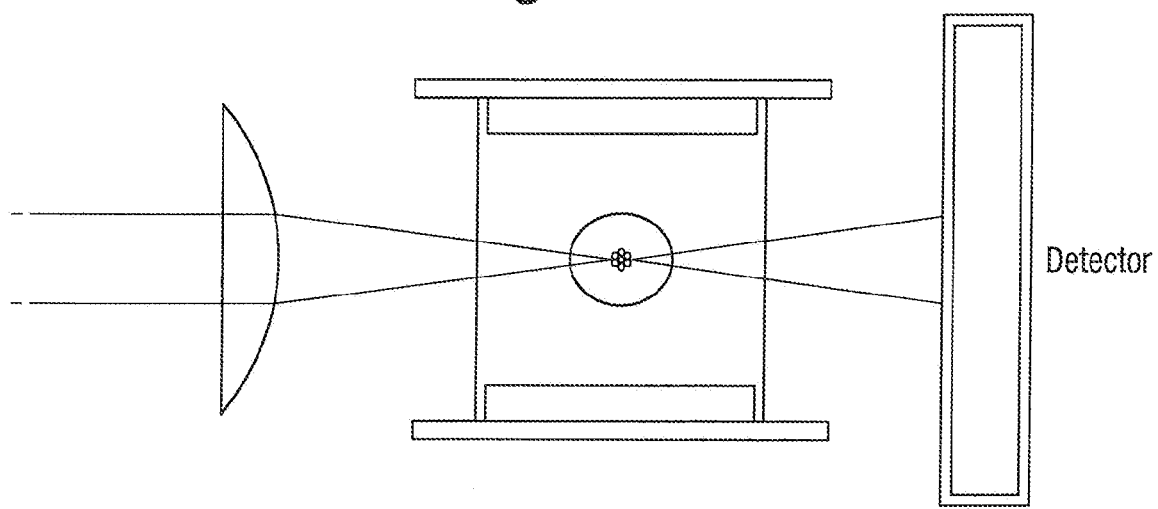
FIG. 11 shows an embodiment of the present invention wherein a light detector is positioned adjacent to an ion guide, opposite to a laser or light source.

According to an another embodiment, the light detector may be used to additionally or alternatively measure the light from the laser or light source. According to this embodiment, the measurement may be used to determine the energy of the light being applied to the ions. FIG. 11 shows an embodiment in which a light detector is positioned adjacent to an ion guide, opposite a laser or light source. According to this embodiment, the light detector is used to measure luminescence from the ions held within the ion guide and/or the energy of the light being applied to the ions.

In some cases, it may be desirable to increase the time during which ions are illuminated in order to increase the probability of reactions between the light and the ions. According to an embodiment, this is done by increasing the length of the path over which ions are illuminated. Alternatively or additionally, ions may be trapped for a time in an illuminated region.

According to this embodiment, ions may be held radially along the axis of a travelling wave device or ion guide which comprises a plurality of electrodes each having an aperture through which ions are transmitted in use. A DC or AC pseudo-potential axial trapping potential is preferably applied to the electrodes in order to trap ions for the desired amount of time while they are illuminated. According to an embodiment, the trapping potential is formed by applying travelling waves to the travelling wave device or ion guide in opposite directions. A laser or light source is preferably used to illuminate the ions and may be directed along the axial length of the ion guide or may be arranged to intersect the ion beam at an angle.

According to an embodiment of the present invention, light from the laser or other light source may be delivered into the device using one or more optical fibers.

Although the present invention has been described with reference to the preferred embodiments, it will be understood by those skilled in the art that various changes in form and detail may be made without departing from the scope of the invention as set forth in the accompanying claims.

The invention claimed is:

1. A method of mass spectrometry comprising:
directing first photons from a laser onto ions located within a 2D or linear ion guide or ion trap;
scanning the frequency of said first photons;
detecting second photons emitted by said ions; and then
mass analysing said ions using a Time of Flight mass analyser.

2. A method as claimed in claim 1, further comprising directing said first photons in a direction which is substantially co-axial or parallel with a longitudinal axis of said ion guide or ion trap.

3. A method as claimed in claim 1, further comprising determining one or more properties of said ions from detecting said first photons or said second photons.

4. A method of mass spectrometry comprising:
illuminating ions located within a 2D or linear ion guide or ion trap with broadband illumination by directing said broadband illumination in a direction which is substantially co-axial or parallel with a longitudinal axis of said ion guide or ion trap;
scanning a transmission property of an optical filter;
detecting photons transmitted by said optical filter; and then
mass analysing said ions using a Time of Flight mass analyser.

5. A mass spectrometer comprising:
a 2D or linear ion guide or ion trap;
a laser arranged and adapted to direct first photons onto ions located, in use, within said 2D or linear ion guide or ion trap;
a device arranged and adapted to scan or vary a frequency of said first photons;
a detector for detecting second photons emitted by said ions; and
a Time of Flight mass analyser.

6. A mass spectrometer comprising:
a 2D or linear ion guide or ion trap;
a broadband illumination source arranged and adapted to illuminate ions located, in use, within said 2D or linear ion guide or ion trap with broadband illumination by directing said broadband illumination in a direction which is substantially co-axial or parallel with a longitudinal axis of said ion guide or ion trap;
a device arranged and adapted to scan a transmission property of an optical filter;
a detector for detecting photons transmitted by said optical filter; and
a Time of Flight mass analyser.

7. A method comprising:
providing a conjoined ion guide or ion trap comprising: (i) a first ion guide section comprising a plurality of electrodes each having an aperture through which ions are transmitted and wherein a first ion guiding path is formed within said first ion guide section; and (ii) a second ion guide section comprising a plurality of electrodes each having an aperture through which ions are transmitted and wherein a second ion guiding path is formed within said second ion guide section, wherein a radial pseudo-potential barrier is formed between said first ion guiding path and said second ion guiding path; and
directing a laser beam along at least part of an axial length of said first ion guide section and providing a first mirror arranged at a first end of said first ion guide section and a second mirror arranged at a second end of said first ion guide, said first and second mirrors forming an optical resonant cavity within said first ion guide section; or
directing a laser beam along at least part of an axial length of said second ion guide section and providing a first mirror arranged at a first end of said second ion guide section and a second mirror arranged at a second end of said second ion guide section, said first and second mirrors forming an optical resonant cavity within said second ion guide section.

8. A method as claimed in claim 7, further comprising subjecting said ions to photo-dissociation.

9. A method as claimed in claim 7, further comprising performing ion spectroscopy, wherein said laser beam comprises first photons, the method further comprising scanning or varying the frequency of said first photons; and further comprising detecting said first photons or detecting second photons emitted by said ions.

10. A method as claimed in claim 7, further comprising transferring ions radially from said first ion guide section into said second ion guide section by urging ions across said pseudo-potential barrier; or
further comprising transferring ions radially from said second ion guide section into said first ion guide section by urging ions across said pseudo-potential barrier.

11. A mass spectrometer comprising:
a conjoined ion guide or ion trap comprising: (i) a first ion guide section comprising a plurality of electrodes each having an aperture through which ions are transmitted and wherein a first ion guiding path is formed within said first ion guide section; and (ii) a second ion guide section comprising a plurality of electrodes each having an aperture through which ions are transmitted and wherein a second ion guiding path is formed within said second ion guide section, wherein a radial pseudo-potential barrier is formed, in use, between said first ion guiding path and said second ion guiding path; and a device arranged and adapted to direct a laser beam along at least part of an axial length of said first ion guide section, a first mirror arranged at a first end of said first ion guide section and a second mirror arranged at a second end of said first ion guide or ion section, said first and second mirrors forming an optical resonant cavity within said first ion guide section; or a device arranged and adapted to direct a laser beam along at least part of an axial length of said second ion guide section, a first mirror arranged at a first end of said second ion guide section and a second mirror arranged at a second end of said second ion guide section, said first and second mirrors forming an optical resonant cavity within said second ion guide section.

12. An ion guide or ion trap comprising:

a first mirror arranged at a first end of said ion guide or ion trap and a second mirror arranged at a second end of said ion guide or ion trap, said first and second mirrors forming an optical resonant cavity along a longitudinal axis of said ion guide or ion trap;

wherein an optical path of the optical resonant cavity is substantially co-axial with the longitudinal axis of the ion guide or ion trap.

13. A photo-dissociation device or a photo-activation device comprising:

an ion guide or ion trap including:

a first mirror arranged at a first end of said ion guide or ion trap and a second mirror arranged at a second end of said ion guide or ion trap, said first and second mirrors forming an optical resonant cavity along a longitudinal axis of said ion guide or ion trap;

wherein an optical path of the optical resonant cavity is substantially co-axial with the longitudinal axis of the ion guide or ion trap.

14. A method comprising:

providing an ion guide or ion trap;

providing a first mirror arranged at a first end of said ion guide or ion trap and a second mirror arranged at a second end of said ion guide or ion trap, wherein said first and second mirrors form an optical resonant cavity along a longitudinal axis of said ion guide or ion trap;

wherein an optical path of the optical resonant cavity is substantially co-axial with the longitudinal axis of the ion guide or ion trap.

15. A method of photo-dissociation or photo-activation comprising:

providing an ion guide or ion trap;

providing a first mirror arranged at a first end of said ion guide or ion trap and a second mirror arranged at a second end of said ion guide or ion trap, wherein said first and second mirrors form an optical resonant cavity along a longitudinal axis of said ion guide or ion trap;

wherein an optical path of the optical resonant cavity is substantially co-axial with the longitudinal axis of the ion guide or ion trap.

16. A mass spectrometer as claimed in claim 5, further comprising a control system arranged and adapted to determine one or more properties of said ions from detecting said first photons or said second photons.

* * * * *